US011045137B2

(12) United States Patent
Barbre et al.

(10) Patent No.: US 11,045,137 B2
(45) Date of Patent: Jun. 29, 2021

(54) METHODS AND APPARATUS FOR IMPROVED SIGNAL ROBUSTNESS FOR A WEARABLE NEUROMUSCULAR RECORDING DEVICE

(71) Applicant: Facebook Technologies, LLC, Menlo Park, CA (US)

(72) Inventors: Curtis Barbre, Brooklyn, NY (US); Jonathan Reid, Brooklyn, NY (US); Ning Guo, Brooklyn, NY (US); Brandon Pool, New York, NY (US)

(73) Assignee: Facebook Technologies, LLC, Menlo Park, CA (US)

( * ) Notice: Subject to any disclaimer, the term of this patent is extended or adjusted under 35 U.S.C. 154(b) by 74 days.

(21) Appl. No.: 16/516,777

(22) Filed: Jul. 19, 2019

(65) Prior Publication Data

US 2020/0022606 A1 Jan. 23, 2020

Related U.S. Application Data

(60) Provisional application No. 62/700,434, filed on Jul. 19, 2018.

(51) Int. Cl.
*A61B 5/00* (2006.01)
*A61B 5/389* (2021.01)

(52) U.S. Cl.
CPC ............ *A61B 5/389* (2021.01); *A61B 5/6801* (2013.01); *A61B 2560/0406* (2013.01); *A61B 2562/04* (2013.01)

(58) Field of Classification Search
CPC ... A61B 5/0488; A61B 5/6801; A61B 5/6802; A61B 5/6803; A61B 5/0476;
(Continued)

(56) References Cited

U.S. PATENT DOCUMENTS 4,055,168 A 10/1977 Miller et al.
4,896,120 A 1/1990 Kamil
(Continued)

FOREIGN PATENT DOCUMENTS

CA 2902045 A1 8/2014
CA 2921954 A1 2/2015
(Continued)

OTHER PUBLICATIONS

PCT/US2017/043686, dated Oct. 6, 2017, International Search Report and Written Opinion.
(Continued)

*Primary Examiner* — Eun Hwa Kim
*Assistant Examiner* — Adam Z Minchella
(74) *Attorney, Agent, or Firm* — FisherBroyles, LLP

(57) ABSTRACT

Arrangements for improving neuromuscular recording electrode contact with a body surface are described. According to some aspects, a sensor assembly may include a housing and one or more electrodes that are moveable relative to the housing. The electrodes may rotate and/or translate relative to the housing and/or have at least two degrees of freedom relative to the housing. The sensor may include a spring element that stores potential energy and biases the electrodes toward a starting position in which the electrodes extend at least partially out of the sensor housing. In some embodiments, application of a contact force to one or more of the electrodes of the sensor compresses the spring element, causing the spring element to store potential energy.

24 Claims, 11 Drawing Sheets

(58) Field of Classification Search
CPC .............. A61B 5/683; A61B 5/6835; A61B 2560/0406; A61B 2562/04; H05K 5/0226; H05K 5/0204
See application file for complete search history.

(56) References Cited

U.S. PATENT DOCUMENTS

| | | | |
|---|---|---|---|
| 5,625,577 A | 4/1997 | Kunii et al. |
| 6,005,548 A | 12/1999 | Latypov et al. |
| 6,009,210 A | 12/1999 | Kand |
| 6,244,873 B1 | 6/2001 | Hill et al. |
| 6,411,843 B1 | 6/2002 | Zarychta |
| 6,658,287 B1 | 12/2003 | Litt et al. |
| 6,720,984 B1 | 4/2004 | Jorgensen et al. |
| 6,774,885 B1 | 8/2004 | Even-Zohar |
| 6,942,621 B2 | 9/2005 | Avinash et al. |
| 7,089,148 B1 | 8/2006 | Bachmann et al. |
| 7,351,975 B2 | 4/2008 | Brady et al. |
| 7,574,253 B2 | 8/2009 | Edney et al. |
| 7,580,742 B2 | 8/2009 | Tan et al. |
| 7,787,946 B2 | 8/2010 | Stahmann et al. |
| 7,805,386 B2 | 9/2010 | Greer |
| 7,901,368 B2 | 3/2011 | Flaherty et al. |
| 8,170,656 B2 | 5/2012 | Tan et al. |
| 8,190,249 B1 | 5/2012 | Gharieb et al. |
| 8,311,623 B2 | 11/2012 | Sanger |
| 8,351,651 B2 | 1/2013 | Lee |
| 8,421,634 B2 | 4/2013 | Tan et al. |
| 8,435,191 B2 | 5/2013 | Barboutis et al. |
| 8,437,844 B2 | 5/2013 | Syed Momen et al. |
| 8,447,704 B2 | 5/2013 | Tan et al. |
| 8,484,022 B1 | 7/2013 | Vanhoucke |
| 8,718,980 B2 | 5/2014 | Garudadri et al. |
| 8,744,543 B2 | 6/2014 | Li et al. |
| 8,754,862 B2 | 6/2014 | Zaliva |
| D717,685 S | 11/2014 | Bailey et al. |
| 8,880,163 B2 | 11/2014 | Barachant et al. |
| 8,890,875 B2 | 11/2014 | Jammes et al. |
| 8,892,479 B2 | 11/2014 | Tan et al. |
| 9,037,530 B2 | 5/2015 | Tan et al. |
| D742,272 S | 11/2015 | Bailey et al. |
| 9,218,574 B2 | 12/2015 | Phillipps et al. |
| 9,235,934 B2 | 1/2016 | Mandella et al. |
| 9,240,069 B1 | 1/2016 | Li |
| 9,278,453 B2 | 3/2016 | Assad |
| 9,299,248 B2 | 3/2016 | Lake et al. |
| D756,359 S | 5/2016 | Bailey et al. |
| 9,351,653 B1 | 5/2016 | Harrison |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,408,316 B2 | 8/2016 | Bailey et al. |
| 9,459,697 B2 | 10/2016 | Bedikian et al. |
| 9,483,123 B2 | 11/2016 | Aleem et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 2003/0144829 A1 | 7/2003 | Geatz et al. |
| 2003/0171921 A1 | 9/2003 | Manabe et al. |
| 2003/0184544 A1 | 10/2003 | Prudent |
| 2004/0054273 A1* | 3/2004 | Finneran ............ A61B 5/389 600/393 |
| 2004/0092839 A1 | 5/2004 | Shin et al. |
| 2006/0129057 A1 | 6/2006 | Maekawa et al. |
| 2007/0009151 A1 | 1/2007 | Pittman et al. |
| 2007/0172797 A1 | 7/2007 | Hada et al. |
| 2007/0177770 A1 | 8/2007 | Derchak et al. |
| 2007/0256494 A1 | 11/2007 | Nakamura et al. |
| 2007/0285399 A1 | 12/2007 | Lund |
| 2008/0051673 A1 | 2/2008 | Kong et al. |
| 2008/0052643 A1 | 2/2008 | Ike et al. |
| 2008/0103639 A1 | 5/2008 | Troy et al. |
| 2008/0214360 A1 | 9/2008 | Stirling et al. |
| 2008/0221487 A1 | 9/2008 | Zohar et al. |
| 2009/0027337 A1 | 1/2009 | Hildreth |
| 2009/0079813 A1 | 3/2009 | Hildreth |
| 2009/0082692 A1 | 3/2009 | Hale et al. |
| 2009/0082701 A1 | 3/2009 | Zohar et al. |
| 2009/0112080 A1 | 4/2009 | Matthews |
| 2009/0124881 A1 | 5/2009 | Rytky |
| 2009/0326406 A1 | 12/2009 | Tan et al. |
| 2009/0327171 A1 | 12/2009 | Tan et al. |
| 2010/0030532 A1 | 2/2010 | Arora et al. |
| 2010/0063794 A1 | 3/2010 | Hernandez-Rebollar |
| 2010/0106044 A1 | 4/2010 | Linderman |
| 2010/0113910 A1 | 5/2010 | Brauers et al. |
| 2010/0280628 A1 | 11/2010 | Sankai |
| 2010/0292595 A1* | 11/2010 | Paul ............... A61B 5/332 600/509 |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0315266 A1 | 12/2010 | Gunawardana et al. |
| 2011/0077484 A1 | 3/2011 | Van Slyke et al. |
| 2011/0092826 A1 | 4/2011 | Lee et al. |
| 2011/0173204 A1 | 7/2011 | Murillo et al. |
| 2011/0173574 A1 | 7/2011 | Clavin et al. |
| 2011/0230782 A1 | 9/2011 | Bartol et al. |
| 2012/0066163 A1 | 3/2012 | Balls et al. |
| 2012/0188158 A1 | 7/2012 | Tan et al. |
| 2012/0265480 A1 | 10/2012 | Oshima |
| 2012/0283526 A1 | 11/2012 | Gommesen et al. |
| 2013/0004033 A1 | 1/2013 | Trugenberger |
| 2013/0077820 A1 | 3/2013 | Marais et al. |
| 2013/0123656 A1 | 5/2013 | Heck |
| 2013/0141375 A1 | 6/2013 | Ludwig et al. |
| 2013/0207889 A1 | 8/2013 | Chang et al. |
| 2013/0217998 A1 | 8/2013 | Mahfouz et al. |
| 2013/0232095 A1 | 9/2013 | Tan et al. |
| 2013/0317382 A1 | 11/2013 | Le |
| 2013/0317648 A1 | 11/2013 | Assad |
| 2014/0052150 A1 | 2/2014 | Taylor et al. |
| 2014/0092009 A1 | 4/2014 | Yen et al. |
| 2014/0098018 A1 | 4/2014 | Kim et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0223462 A1 | 8/2014 | Aimone et al. |
| 2014/0240103 A1 | 8/2014 | Lake et al. |
| 2014/0240223 A1 | 8/2014 | Lake et al. |
| 2014/0245200 A1 | 8/2014 | Holz |

(56) References Cited

U.S. PATENT DOCUMENTS

| | | |
|---|---|---|
| 2014/0249397 A1 | 9/2014 | Lake et al. |
| 2014/0277622 A1 | 9/2014 | Raniere |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0330404 A1 | 11/2014 | Abdelghani et al. |
| 2014/0334083 A1 | 11/2014 | Bailey |
| 2014/0344731 A1 | 11/2014 | Holz |
| 2014/0355825 A1 | 12/2014 | Kim et al. |
| 2014/0358024 A1 | 12/2014 | Nelson et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1* | 1/2015 | Bailey .................... H05K 7/026 600/390 |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1* | 5/2015 | Morun .................... H05K 1/162 600/372 |
| 2015/0157944 A1 | 6/2015 | Gottlieb |
| 2015/0169074 A1 | 6/2015 | Ataee et al. |
| 2015/0182165 A1* | 7/2015 | Miller .................... A61B 5/486 600/544 |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1 | 2/2016 | Lee |
| 2016/0092504 A1 | 3/2016 | Mitri et al. |
| 2016/0144172 A1 | 5/2016 | Hsueh et al. |
| 2016/0162604 A1 | 6/2016 | Xioli et al. |
| 2016/0187992 A1 | 6/2016 | Yamamoto et al. |
| 2016/0235323 A1 | 8/2016 | Tadi et al. |
| 2016/0239080 A1 | 8/2016 | Marcolina et al. |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068445 A1 | 3/2017 | Lee et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1 | 6/2017 | Oono et al. |
| 2017/0188980 A1 | 7/2017 | Ash |
| 2017/0259167 A1 | 9/2017 | Cook et al. |
| 2017/0285756 A1 | 10/2017 | Wang et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2017/0344706 A1 | 11/2017 | Tones et al. |
| 2017/0347908 A1 | 12/2017 | Watanabe et al. |
| 2018/0000367 A1 | 1/2018 | Longinotti-Buitoni |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0081439 A1 | 3/2018 | Daniels |
| 2018/0088765 A1 | 3/2018 | Bailey |
| 2018/0092599 A1* | 4/2018 | Kerth .................... A42B 1/242 |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0178008 A1 | 6/2018 | Bouton et al. |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |
| 2019/0324549 A1 | 10/2019 | Araki et al. |
| 2019/0357787 A1 | 11/2019 | Barachant et al. |
| 2019/0362557 A1 | 11/2019 | Lacey et al. |

FOREIGN PATENT DOCUMENTS

| | | |
|---|---|---|
| CA | 2939644 A1 | 8/2015 |
| CN | 1838933 A | 9/2006 |
| CN | 103777752 A | 5/2014 |
| CN | 105190578 A | 12/2015 |
| CN | 106102504 A | 11/2016 |
| EP | 2198521 B1 | 6/2012 |
| EP | 2959394 A1 | 12/2015 |
| EP | 3104737 A1 | 12/2016 |
| JP | H05-277080 A | 10/1993 |
| JP | 2005-095561 A | 4/2005 |

(56) References Cited

FOREIGN PATENT DOCUMENTS

| | | |
|---|---|---|
| JP | 2010-520561 A | 6/2010 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | WO 2008/109248 A2 | 9/2008 |
| WO | WO 2009/042313 A1 | 4/2009 |
| WO | WO 2010/104879 A2 | 9/2010 |
| WO | WO 2012/155157 | 11/2012 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |
| WO | WO 2017/120669 A1 | 7/2017 |
| WO | WO 2017/172185 A1 | 10/2017 |
| WO | WO 2017/208167 | 12/2017 |

OTHER PUBLICATIONS

PCT/2017/043686, dated Feb. 7, 2019, International Preliminary Report on Patentability.
PCT/US2017/043693, dated Oct. 6, 2017, International Search Report and Written Opinion.
PCT/US2017/043693, dated Feb. 7, 2019, International Preliminary Report on Patentability.
PCT/US2017/043791, dated Oct. 5, 2017, International Search Report and Written Opinion.
PCT/US2017/043791, dated Feb. 7, 2019, International Preliminary Report on Patentability.
PCT/US2017/043792, dated Oct. 5, 2017, International Search Report and Written Opinion.
PCT/US2017/043792, dated Feb. 7, 2019, International Preliminary Report on Patentability.
PCT/US2018/056768, dated Jan. 15, 2019, International Search Report and Written Opinion.
PCT/US2018/061409, dated Mar. 12, 2019, International Search Report and Written Opinion.
PCT/US2018/063215, dated Mar. 21, 2019, International Search Report and Written Opinion.
PCt/US2019/015134, dated May 15, 2019, International Search Report and Written Opinion.
PCT/US2019/015167, dated May 21, 2019, International Search Report and Written Opinion.
PCT/US2019/015174, dated May 21, 2019, International Search Report and Written Opinion.
PCT/US2019/015180, dated May 28, 2019, International Search Report and Written Opinion.
PCT/US2019/015183, dated May 3, 2019, International Search Report and Written Opinion.
PCT/US2019/015238, dated May 16, 2019, International Search Report and Written Opinion.
PCT/US2019/015244, dated May 16, 2019, International Search Report and Written Opinion.
PCT/US19/20065, dated May 16, 2019, International Search Report and Written Opinion.
PCT/US2019/028299, dated Aug. 9, 2019 International Search Report and Written Opinion.
PCT/US2019/031114, dated Aug. 6, 2019, Invitation to Pay Additional Fees.
PCT/US2019/034173, dated Sep. 18, 2019, International Search Report and Written Opinion.
PCT/US2019/037302, dated Oct. 11, 2019, International Search Report and Written Opinion.
PCT/US2019/049094, dated Oct. 24, 2019, Invitation to Pay Additional Fees.
International Preliminary Report on Patentability for International Application No. PCT/US2017/043686 dated Feb. 7, 2019.
International Search Report and Written Opinion for International Application No. PCT/US2017/043686 dated Oct. 6, 2017.
International Preliminary Report on Patentability for International Application No. PCT/US2017/043693 dated Feb. 7, 2019.
International Search Report and Written Opinion for International Application No. PCT/US2017/043693 dated Oct. 6, 2017.
International Preliminary Report on Patentability for International Application No. PCT/US2017/043791 dated Feb. 7, 2019.
International Search Report and Written Opinion for International Application No. PCT/US2017/043791 dated Oct. 5, 2017.
International Preliminary Report on Patentability for International Application No. PCT/US2017/043792 dated Feb. 7, 2019.
International Search Report and Written Opinion for International Application No. PCT/US2017/043792 dated Oct. 5, 2017.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 28, 2019.
International Search Report and Written Opinion for International Application No. PCT/US2019/015244 dated May 16, 2019.
International Search Report and Written Opinion for International Application No. PCT/US2019/028299 dated Aug. 9, 2019.
International Search Report and Written Opinion for International Application No. PCT/US2019/034173 dated Sep. 18, 2019.
Invitation to Pay Additional Fees for International Application No. PCT/US2019/031114 dated Aug. 6, 2019.
International Search Report and Written Opinion for International Application No. PCT/US19/20065 dated May 16, 2019.
International Search Report and Written Opinion for International Application No. PCT/US2019/037302 dated Oct. 11, 2019.
Invitation to Pay Additional Fees for International Application No. PCT/US2019/049094 dated Oct. 24, 2019.
Arkenbout et al., Robust Hand Motion Tracking through Data Fusion of 5DT Data Glove and Nimble VR Kinect Camera Measurements. Sensors. 2015;15:31644-71.
Benko et al., Enhancing Input on and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Davoodi et al., Development of a Physics-Based Target Shooting Game to Train Amputee Users of Multijoint Upper Limb Prostheses. Presence. Massachusetts Institute of Technology. 2012;21(1):85-95.

(56) References Cited

OTHER PUBLICATIONS

Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.
Gallina et al., Surface EMG Biofeedback. Surface Electromyography: Physiology, Engineering, and Applications. 2016:485-500.
Gopura et al., A Human Forearm and wrist motion assist exoskeleton robot with EMG-based fuzzy-neuro control. Proceedings of the 2nd IEEE/RAS-EMBS International Conference on Biomedical Robotics and Biomechatronics. Oct. 19-22, 2008. 6 pages.
Hauschild et al., A Virtual Reality Environment for Designing and Fitting Neural Prosthetic Limbs. IEEE Transactions on Neural Systems and Rehabilitation Engineering. 2007;15(1):9-15.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.
Lee et al., Motion and Force Estimation System of Human Fingers. Journal of Institute of Control, Robotics and Systems. 2011;17(10):1014-1020.
Li et al., Motor Function Evaluation of Hemiplegic Upper-Extremities Using Data Fusion from Wearable Inertial and Surface EMG Sensors. Sensors. MDPI. 2017;17(582):1-17.
Lopes et al., Hand/arm gesture segmentation by motion using IMU and EMG sensing. ScienceDirect. Elsevier. Procedia Manufacturing. 2017;11:107-13.
Martin et al., A Novel Approach of Prosthetic Arm Control using Computer Vision, Biosignals, and Motion Capture. IEEE. 2014. 5 pages.
McIntee, A Task Model of Free-Space Movement-Based Gestures. Dissertation. Graduate Faculty of North Carolina State University. Computer Science. 2016. 129 pages.
Mendes et al., Sensor Fusion and Smart Sensor in Sports and Biomedical Applications. Sensors. 2016;16(1569):1-31.
Mohamed, Homogeneous cognitive based biometrics for static authentication. Dissertation submitted to University of Victoria, Canada. 2010. 149 pages. URL:http://hdl.handle.net/1828/3211 [last accessed Oct. 11, 2019].
Naik et al., Source Separation and Identification issues in bio signals: A solution using Blind source separation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface Emg decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sartori et al., Neural Data-Driven Musculoskeletal Modeling for Personalized Neurorehabilitation Technologies. IEEE Transactions on Biomedical Engineering. 2016;63(5):879-93.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16. 12 pages.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Valero-Cuevas et al., Computational Models for Neuromuscular Function. Nih Public Access Author Manuscript. Jun. 16, 2011. 52 pages.
Wodzinski et al., Sequential Classification of Palm Gestures Based on A* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.
Yang et al., Surface EMG based handgrip force predictions using gene expression programming. Neurocomputing. 2016;207:568-579.
Extended European Search Report for European Application No. EP 17835111.0 dated Nov. 21, 2019.
Extended European Search Report for European Application No. EP 17835140.9 dated Nov. 26, 2019.
International Search Report and Written Opinion for International Application No. PCT/US2019/042579 dated Oct. 31, 2019.
International Search Report and Written Opinion for International Application No. PCT/US2019/052131 dated Dec. 6, 2019.
International Search Report and Written Opinion for International Application No. PCT/US2019/046351 dated Nov. 7, 2019.
Al-Mashhadany, Inverse Kinematics Problem (IKP) of 6-DOF Manipulator Bgy Locally Recurrent Neural Networks (LRNNs). Management and Service Science (MASS). 2010 International Conference ON, IEEE. Aug. 24, 2010. 5 pages. ISBN: 978-1-4244-5325-2.
Kipke et al., Silicon-substrate Intracortical Microelectrode Arrays for Long-Term Recording of Neuronal Spike Activity in Cerebral Cortex. IEEE Transactions on Neural Systems and Rehabilitation Engineering. 2003;11(2):151-155.
Marcard et al., Sparse Inertial Poser: Automatic 3D Human Pose Estimation from Sparse IMUs. Eurographics. 2017;36(2). 12 pages.
Wittevrongel et al., Spatiotemporal Beamforming: A Transparent and Unified Decoding Approach to Synchronous Visual Brain-Computer Interfacing. Frontiers in Neuroscience. 2017;11:1-12.
Zacharaki et al., Spike pattern recognition by supervised classification in low dimensional embedding space. Informatics. 2016;3:73-8. DOI: 10.1007/s40708-016-0044-4.

* cited by examiner

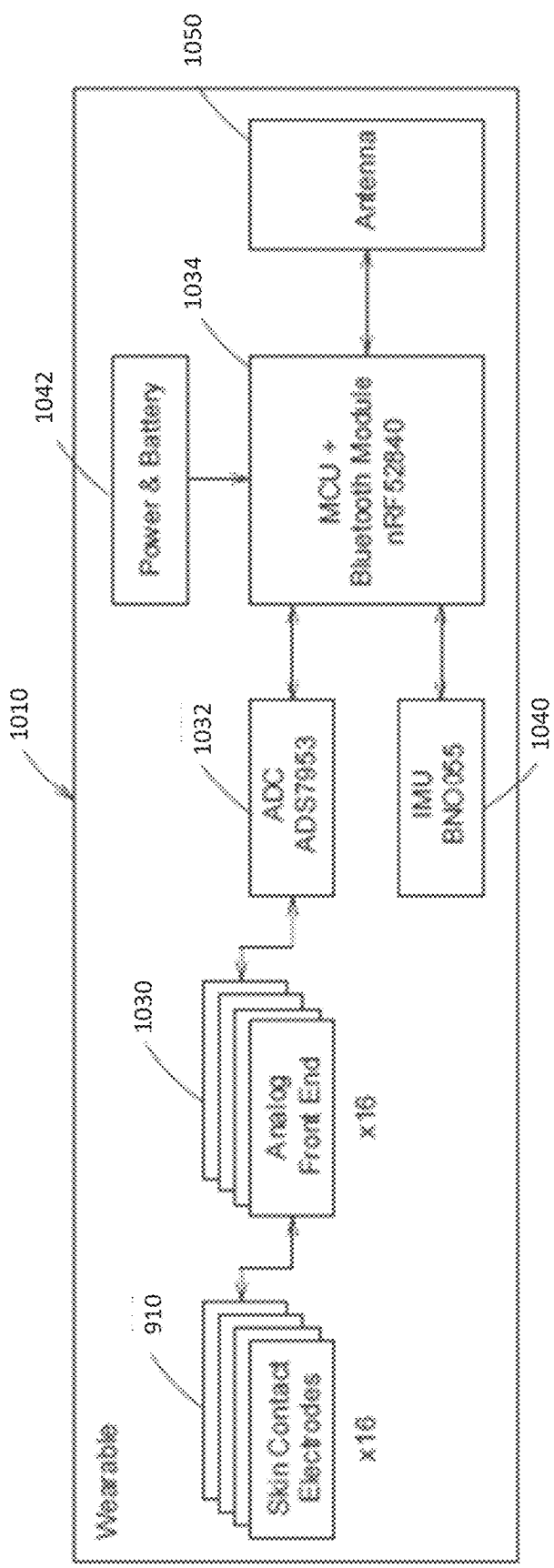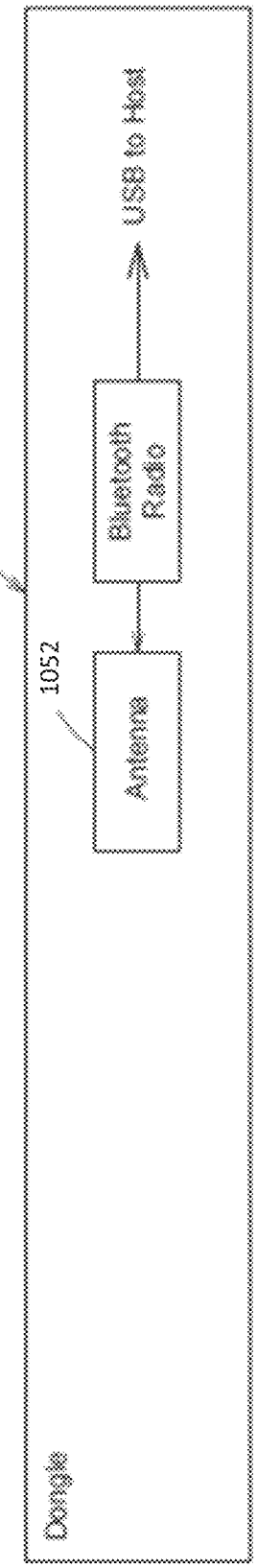
FIG. 10A
FIG. 10B

METHODS AND APPARATUS FOR IMPROVED SIGNAL ROBUSTNESS FOR A WEARABLE NEUROMUSCULAR RECORDING DEVICE

RELATED APPLICATIONS

This application claims priority under 35 U.S.C. § 119(e) to U.S. Provisional Application No. 62/700,434 filed Jul. 19, 2018 and titled, "METHODS AND APPARATUS FOR IMPROVED SIGNAL ROBUSTNESS FOR A WEARABLE NEUROMUSCULAR DEVICE," the entire contents of which is incorporated by reference herein.

BACKGROUND

Neuromuscular signals arising from the human central nervous system may reflect neural activation that results in the contraction of one or more muscles in the human body. Neuromuscular recording sensors, an example of which includes surface electromyography (sEMG) sensors, placed on the surface of the human body record neuromuscular activity produced when skeletal muscle cells are activated. The neuromuscular activity measured by neuromuscular recording sensors may result from neural activation, muscle excitation, muscle contraction, or a combination of the neural activation and muscle excitation and contraction. Signals recorded by neuromuscular recording sensors are routinely used to assess neuromuscular dysfunction in patients with motor control disorders and have been used in some applications as control signals for devices such as prosthetic limbs. High quality surface electromyography (sEMG) signals are typically acquired from wet electrodes in a laboratory setting using skin preparations that require application of a gel or paste at the electrode-skin interface to improve the conductivity between the skin and the electrodes.

SUMMARY

Coordinated movements of skeletal muscles in the human body that collectively result in the performance of a motor task originate with neural signals arising in the central nervous system. The neural signals travel from the central nervous system to muscles via spinal motor neurons, each of which has a cell body in the spinal cord and axon terminals on one or more muscle fibers. In response to receiving the neural signals, the muscle fibers contract resulting in muscle movement. A spinal motor neuron and the muscle fiber(s) it innervates are collectively referred to as a "motor unit." Muscles typically include muscle fibers from hundreds of motor units and simultaneous contraction of muscle fibers in multiple motor units is usually required for muscle contraction that results in movement and forces in the musculoskeletal system.

Neuromuscular recording sensors such as EMG sensors record biological signals that result in motor activity, such as contraction of a muscle. In the case of EMG sensors arranged on the surface of the human body, the biological signals recorded relate to the generation of action potentials in motor units, though the signals are dominated by signals originating from muscle fibers. Some embodiments are directed to analyzing neuromuscular signals to identify patterns of activation associated with sub-muscular biological structures (e.g., individual motor units or groups of motor units). Control signals determined based on activation of muscle groups or sub-muscular structures may be used to control the operation of devices.

According to some aspects, a wearable bioelectrical sensing device is provided. The wearable bioelectrical sensing device comprises a plurality of electrodes including a first electrode, a second electrode, a third electrode, and a fourth electrode. The wearable bioelectrical sensing device further comprises a first housing containing at least a portion of the first electrode and at least a portion of the second electrode, each of the first and second electrode being configured to rotate relative to the first housing from a starting position to a rotated position, and a second housing containing at least a portion of the third electrode and at least a portion of the fourth electrode, each of the third and fourth electrodes being configured to rotate relative to the second housing, wherein the first housing and the second housing are coupled to each other in an arrangement that enables the first, second, third, and fourth electrode to contact a body part of a user when the wearable bioelectrical sensing device is worn around the body part of the user. The wearable bioelectrical sensing device further comprises a first flexible circuit electrically connecting the first electrode to the second electrode within the first housing, a second flexible circuit electrically connecting the third electrode to the fourth electrode within the second housing, and a spring element configured to bias the first electrode toward the starting position of the first electrode.

According to some aspects, a wearable bioelectrical sensing device is provided. The wearable bioelectrical sensing device comprises a plurality of electrodes including a first electrode, a second electrode, a third electrode, and a fourth electrode. The wearable bioelectrical sensing device further comprises a first housing containing at least a portion of the first electrode and at least a portion of the second electrode, each of the first and second electrodes being movable relative to the first housing with at least one degree of freedom such that each of the first electrode and second electrode is movable from a starting position to a different position relative to the first housing. The wearable bioelectrical sensing device further comprises a second housing containing at least a portion of the third electrode and at least a portion of the fourth electrode, each of the third and fourth electrodes being movable relative to the second housing with at least one degree of freedom such that each of the third electrode and the fourth electrode is movable from a starting position to a different position relative to the second housing, wherein the first housing and the second housing are coupled to each other in an arrangement that enables the first, second, third, and fourth electrode to contact a body part of a user when the wearable bioelectrical sensing device is worn around the body part of the user. The wearable bioelectrical sensing device further comprises, a first flexible circuit electrically connecting the first electrode to the second electrode within the first housing, a second flexible circuit electrically connecting the third electrode to the fourth electrode within the second housing, and a spring element configured to bias the first electrode toward the starting position of the first electrode.

According to some aspects, a method of using a wearable bioelectrical sensing device is provided. The method comprises wearing the wearable bioelectrical sensing device to contact a first electrode, a second electrode, a third electrode, and a fourth electrode of the device with skin, wherein the wearable bioelectrical sensing device includes a first housing containing at least a portion of the first electrode and at least a portion of the second electrode, and a second housing containing at least a portion of the third electrode and at least a portion of the fourth electrode, and rotating the first electrode relative to the first housing from a starting position to a rotated position while keeping the first electrode in contact with the skin throughout the rotation.

According to some aspects, a method of using a wearable bioelectrical sensing device is provided. The method comprises wearing the wearable bioelectrical sensing device to contact a first electrode, a second electrode, a third electrode, and a fourth electrode of the device with skin, wherein the wearable bioelectrical sensing device includes a first housing containing at least a portion of the first electrode and at least a portion of the second electrode, and a second housing containing at least a portion of the third electrode and at least a portion of the fourth electrode, and moving the first electrode relative to the first housing with at least two degrees of freedom from a starting position to a different position.

According to some aspects, a wearable device is provided, including a first electrode and a first housing containing at least a portion of the first electrode. The first electrode is configured to rotate relative to the first housing from a starting position to a rotated position. The wearable device also includes a band that is coupled to the first housing and is configured to be worn by a user.

According to some aspects, a wearable device is provided, including a first electrode and a first housing containing at least a portion of the first electrode. The first electrode is movable relative to the first housing with at least two degrees of freedom such that the first electrode is movable from a starting position to a different position relative to the first housing. The wearable device also includes a band that is coupled to the first housing and is configured to be worn by a user.

According to some aspects, a method of using a wearable device is provided, including: wearing a band to contact a first electrode with skin, where a first housing is coupled to the band and the first housing contains at least a portion of the first electrode, and rotating the first electrode relative to the first housing from a starting position to a rotated position.

According to some aspects, a method of using a wearable device is provided, including: wearing a band to contact a first electrode with skin, where a first housing is coupled to the band and the first housing contains at least a portion of the first electrode, and moving the first electrode relative to the first housing with at least two degrees of freedom from a starting position to a different position.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

FIGS. 10A and 10B schematically illustrate components of a computer-based system on which some embodiments are implemented. FIG. 10A illustrates a wearable portion of the computer-based system and FIG. 10B illustrates a dongle portion connected to a computer, wherein the dongle portion is configured to communicate with the wearable portion;

DETAILED DESCRIPTION

Figure 1:
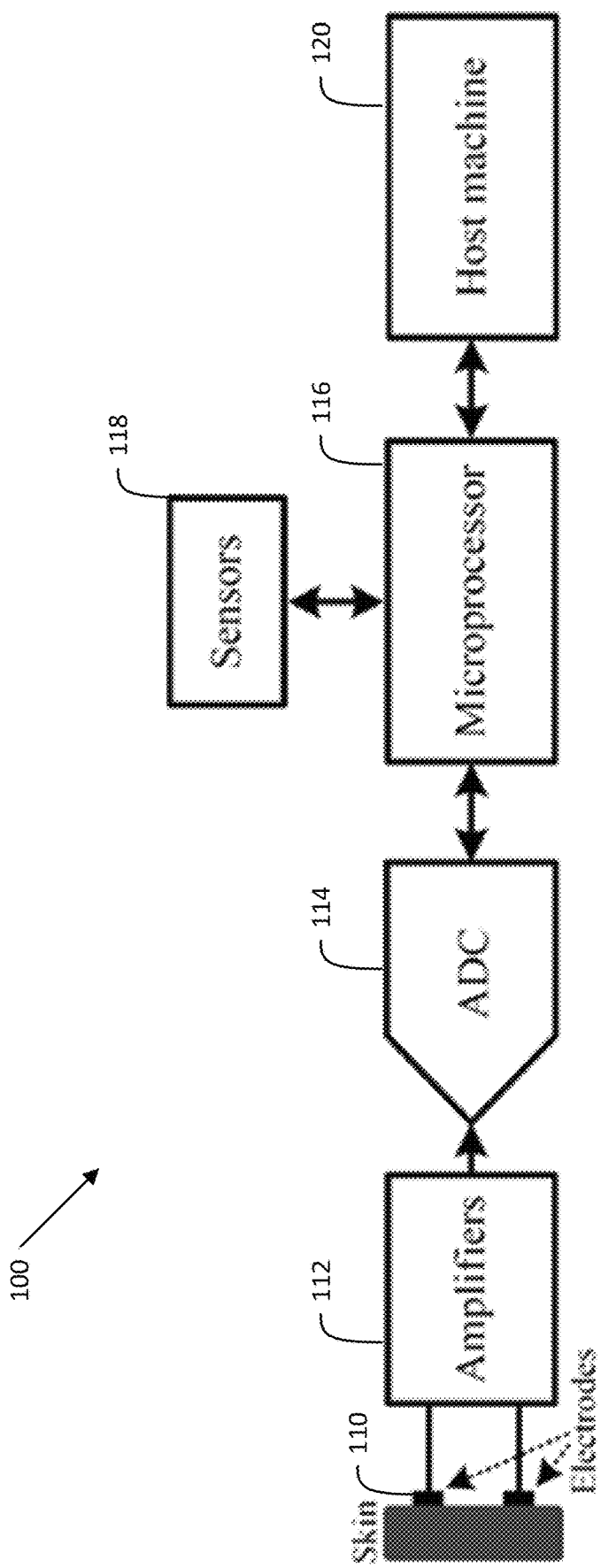
FIG. 1 is a schematic diagram of components of a neuromuscular recording system in accordance with some embodiments of the technology described herein.

Obtaining consistent high-quality neuromuscular (e.g., sEMG) signals using neuromuscular recording (e.g., sEMG) electrodes and conventional signal processing techniques is challenging, in part due to the difficulty of maintaining sufficient contact between a neuromuscular recording electrode and a moving body surface, e.g., skin.

Aspects herein relate to the use of sensors to detect biological signals resulting from the activation of motor unit. The sensors may include a plurality of neuromuscular recording sensors configured to detect signals arising from neuromuscular activity in skeletal muscle of a human body. The term "neuromuscular activity" as used herein refers to neural activation of spinal motor neurons that innervate a muscle, muscle activation, muscle contraction, or any combination of neural activation, muscle activation, and muscle contraction. In some embodiments, the plurality of neuromuscular recording sensors may be used to sense sub-muscular activity associated with a sub-muscular structure (e.g., a motor unit or set of motor units). In various embodiments of the systems, apparatuses, and methods described herein, neuromuscular signals may be used to derive control signals for machine control, to create an immersive rendering of a virtual hand (e.g., a rendering of the user's 'hand-state'), or other applications. In general, consistent and high-quality neuromuscular signals (e.g., high signal-to-noise ratio (SNR), consistent noise characteristics in the frequency-domain, etc.) enable the neuromuscular signals to be more effectively used for immersive, control, and other applications. The inventors have recognized that in at least some instances, motion artifacts may cause an epoch of recorded data to be unsatisfactory or unusable (e.g., on one or more channels of a neuromuscular recording sensor array) due to the magnitude of the artifact being larger than the biological signals of interest. Motion artifacts may change the baseline (e.g., direct current level) of a recording. In some instances, motion artifacts may cause an amplifier in a neuromuscular recording system to saturate, rendering the underlying biological signal completely unresolvable.

To detect signals arising from neuromuscular activity, neuromuscular recording electrodes are held in contact against a body surface (e.g., skin). When the contact between skin and an electrode changes, motion artifacts may be generated. For example, an electrode may partially or fully lift off of the skin due to movement of a wearable neuromuscular recording device and/or conformational changes in a user's body due to movement, muscle contraction, or other reason. Motion artifacts may also be generated from a change in the pressure between electrode and skin, a change of the orientation (e.g., an angle as parametrized by pitch, yaw, and roll) of an electrode relative to the skin, a translation of the electrode (e.g., a change in the position of the electrode on the skin), or a conformational change in the tissue underlying the electrode due to a muscle contraction, movement, or other reason.

Dry biosensor electrodes that interface mechanically with skin for recording neuromuscular activity are preferred relative to electrodes that require the use of adhesive and/or conductive gels (i.e., 'wet electrodes'). Compared to wet electrodes, dry electrodes require less set up time, can be re-used numerous times without degrading signal quality, and provide a more pleasant user experience due to the absence of residue on the skin after an electrode has been removed. The inventors have appreciated that dry electrodes or those that interface with a body surface without the use of adhesive and/or conductive gels are susceptible to signal variations—in part due to several kinds of motion artifacts—that make downstream processing of biological signals challenging. For example, the neuromuscular recording sensors (i.e., electrodes) may interface with a part of the body that changes in size and cross-section during muscle contractions, or the electrodes may be integrated in a wearable form factor that shifts relative to the skin due to movements and forces of a user's musculoskeletal system. For example, as the body part changes conformation, the electrodes may lift off of the body part surface (fully or partially), become further pressed into the surface (possibly changing the impedance of the skin-electrode contact), shift laterally across the skin, or otherwise experience a change in the recording contact with the skin.

The inventors have recognized that variable pressure across electrodes can cause inaccuracies and motion artifacts. The inventors have also appreciated that an electrode lifting off the body surface may permit electrical line noise (e.g., 50 Hz or 60 Hz noise) to completely infiltrate the signal, reducing the fidelity of the neuromuscular recordings.

The inventors have also recognized that body hair can contribute to reduced quality of neuromuscular recordings because hair between the electrode surface and the skin is not conductive, which may have one or more deleterious effects on the quality of neuromuscular signals, including: increased noise (e.g., electrical line noise) and a propensity for exacerbated motion artifacts when the hairs between an electrode and the skin shift or otherwise change in position and/or composition.

The inventors have observed that epochs of poor signal quality in neuromuscular recordings often coincide with muscle contractions that cause the body surface to pull away from the electrode surface. Mechanical or other strategies to maintain a consistent electrode-skin interface for neuromuscular recording despite conformational changes or movement of a user's body would improve the quality and consistency of neuromuscular recordings.

In addition to signal variations due to hair or movement of the subject's skin and muscle, the inventors have also recognized that movement of the housing or other component of a wearable neuromuscular recording apparatus mechanically coupled to a neuromuscular recording sensor (e.g., an sEMG electrode) may impart an inertial moment at the electrode-skin interface and can likewise cause motion artifacts in the recorded neuromuscular signals.

In addition to being undesirable in the resulting signal, the inventors have also recognized that large artifacts and shifts in the baseline of a signal often dictate choice of an amplifier gain and filter components such that the amplifier will not saturate and/or will recover quickly. Reducing motion artifacts, electrode contact issues, 50 or 60 Hz noise, and amplifier saturation allows for more flexibility in the choice of circuit components and allows for use of a larger portion of the ADC (analog digital converter) dynamic range for biosignal recording, resulting in finer resolution/precision in the neuromuscular (e.g., sEMG) signal output from a recording system such as that shown in FIG. 1 and FIGS. 10A-B.

In some clinical applications, wet contact electrodes containing a hydrogel or other conductive material at the dermal surface are often used in combination with adhesive pads for signal stability. The inventors have appreciated that these electrodes can be time consuming to apply and are usually single use due to the degradation of the hydrogel (or other 'wet') interface and adhesive due to dirt and oils on the skin. The inventors have also recognized that, in some clinical applications, semi-dry electrodes are used instead of wet contact electrodes. The inventors have appreciated that, while semi-dry electrodes are not typically applied with adhesive and may be multi-use, they may require maintenance, proper storage, and can be less durable than a dry electrode.

The inventors have thus recognized the need for an arrangement that provides improved contact between electrodes for neuromuscular and other biosignal recording and a user's body surface. The systems and methods described herein may be used for any bioelectrical surface recording, including neuromuscular recordings (e.g., electromyography, electrical impedance tomography) and other biosignal recordings.

FIG. 1 schematically depicts components of an illustrative neuromuscular recording system 100, in accordance with some embodiments. System 100 includes a pair of neuromuscular recording (e.g., dry sEMG) electrodes 110. In some embodiments, electrodes 110 may be arranged as a portion of a wearable device configured to be worn on or around a part of a user's body. For example, in one non-limiting example, a plurality of neuromuscular recording sensors including neuromuscular recording electrodes (e.g., electrodes 110) are arranged circumferentially around an adjustable and/or elastic band such as a wristband or armband configured to be worn around a user's wrist or arm. Alternatively, at least some of the neuromuscular recording sensors may be arranged on a wearable patch configured to be affixed to a portion of the user's body.

Surface potentials recorded by neuromuscular recording electrodes are typically small (µV to mV) and amplification of the signals recorded by the neuromuscular recording electrodes is typically desired. As shown in FIG. 1, neuromuscular recording (e.g., dry sEMG) electrodes 110 are coupled to amplification circuitry 112, configured to amplify the neuromuscular signals recorded by the electrodes. The output of the amplification circuitry 112 is provided to analog-to-digital converter (ADC) circuitry 114, which converts the amplified neuromuscular signals to digital signals for further processing by microprocessor 116. Microprocessor 116 may be implemented by one or more hardware processors. The processed signals output from microprocessor 116 may be interpreted by host machine 120, examples of which include, but are not limited to, a desktop computer, a laptop computer, a smartwatch, a smartphone, or any other computing device. In some implementations, host machine 120 may be configured to output one or more control signals for controlling a physical or virtual device based, at least in part, on an analysis of the signals output from microprocessor 116.

As shown, neuromuscular recording system 100 also includes sensors 118, which may be configured to record types of information about a state of a user other than neuromuscular information. For example, sensors 118 may include, but are not limited to, temperature sensors configured to measure skin/electrode temperature, inertial measurement unit (IMU) sensors configured to measure movement information such as rotation and acceleration, humidity sensors, heart-rate monitor sensors, camera and video input, and other bio-chemical sensors configured to provide information about the user and/or the user's environment.

Figure 2:
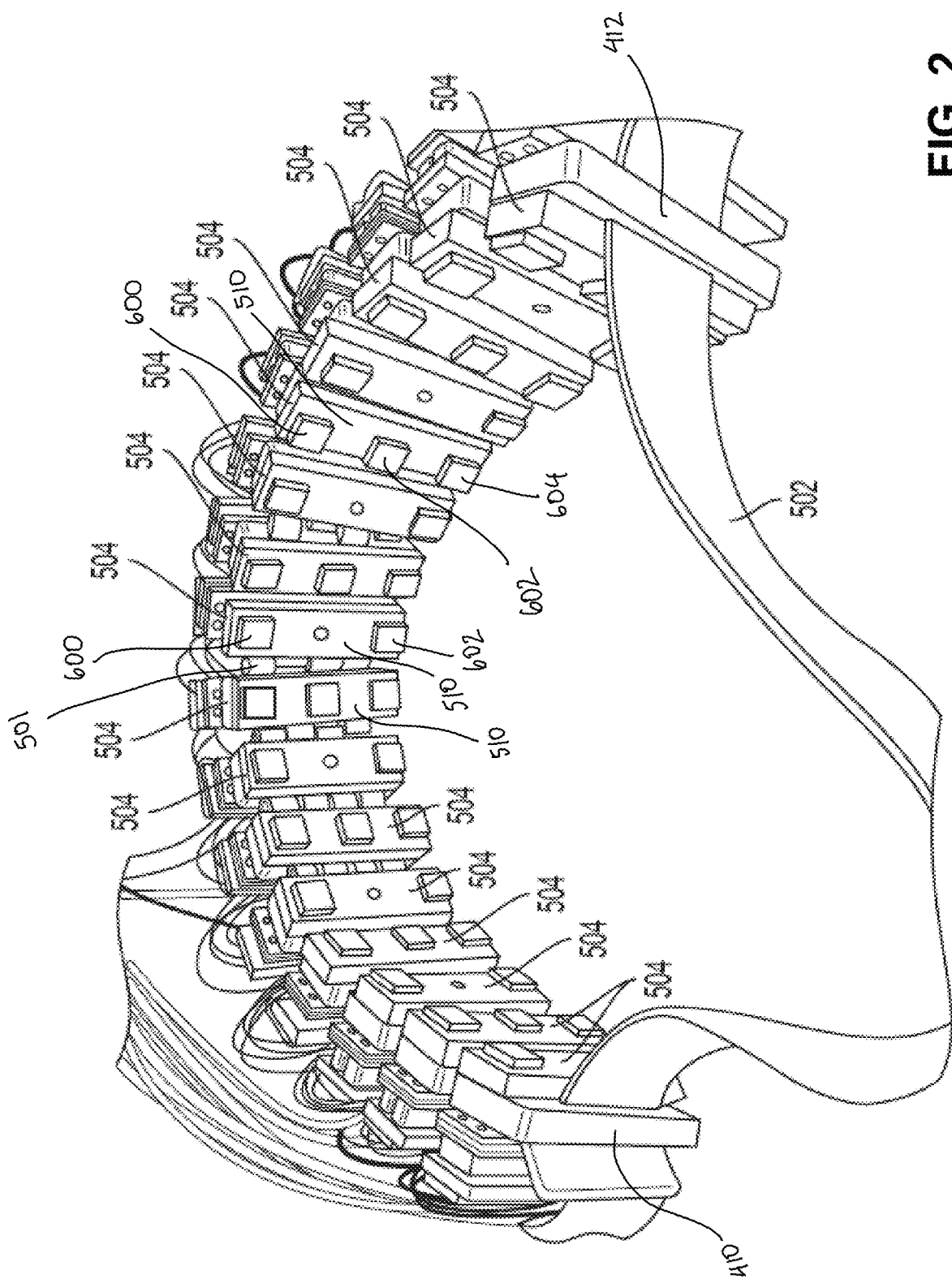
FIG. 2 illustrates a wristband having neuromuscular recording sensors arranged circumferentially thereon, in accordance with some embodiments of the technology described herein.

In one implementation, sixteen neuromuscular recording sensors including neuromuscular recording (e.g., dry sEMG) electrodes are arranged circumferentially around an elastic band configured to be worn around a body part, such as a user's lower arm. For example, FIG. 2 shows neuromuscular recording sensors 504 coupled to a band 502, which may be an elastic band. The sensors may be arranged circumferentially around the band. It should be appreciated that any suitable number of neuromuscular recording sensors having any suitable number of neuromuscular recording (e.g., dry sEMG) electrodes may be used and the number and arrangement of sensors/electrodes may depend on the particular application for which the wearable device is used. For example, as shown in FIG. 2, some of the neuromuscular recording sensors 504 include two neuromuscular recording electrodes 600 and 602, whereas others of the neuromuscular recording sensors 504 include three neuromuscular recording electrodes 600, 602, and 604, with the middle of the three electrodes being a ground or reference electrode. The ground electrode may be included on one or more of the neuromuscular recording sensors 504 to, for example, further bias the skin potential and/or to filter out noise. Each of the sensors 504 may include a sensor housing 510. Although the schematic diagram in FIG. 1 illustrates only two or three electrodes being connected to an amplifier, it should be appreciated that for sEMG sensors 504 in which one, two, three, or more than three electrodes are used, a corresponding number of connections between the electrodes and the amplification circuitry would be included.

Figure 3:
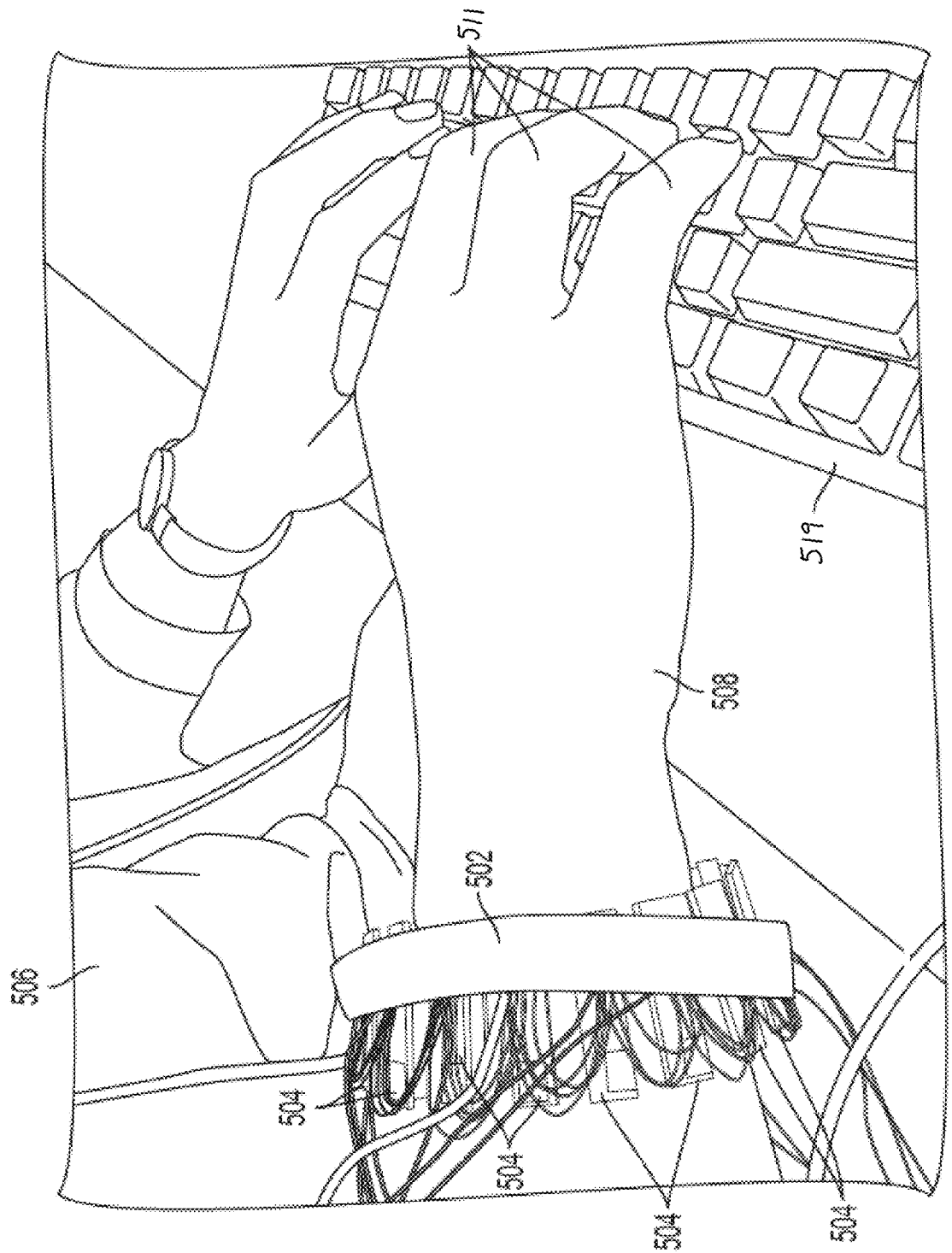
FIG. 3 illustrates a user wearing the wristband of FIG. 2 while typing on a keyboard, in accordance with some embodiments of the technology described herein.

In one example application of the technology described herein, FIG. 3 shows a user 506 wearing elastic band 502 on hand 508. In this way, neuromuscular recording sensors 504 may be configured to record neuromuscular signals as a user controls keyboard 519 using fingers 511.

Figure 9A:
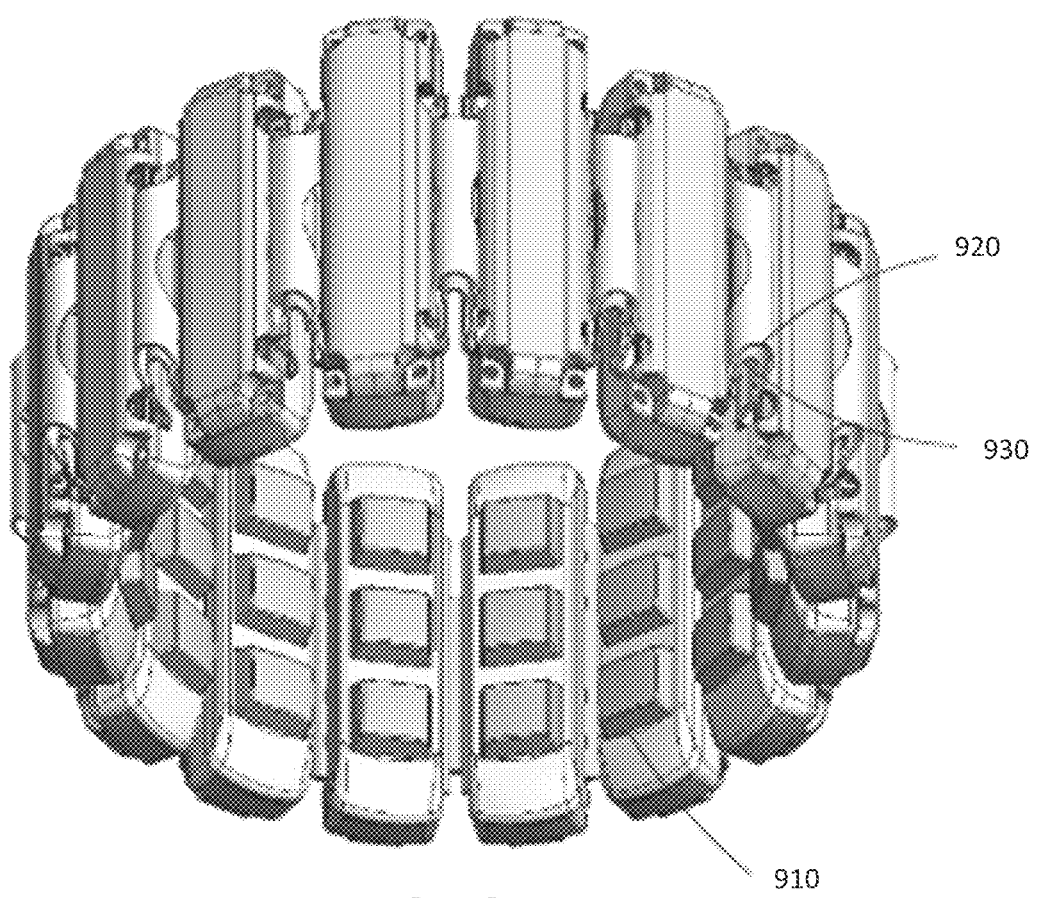
FIG. 9A illustrates a wearable system with sixteen neuromuscular recording sensors arranged circumferentially around an elastic band configured to be worn around a user's lower arm or wrist, in accordance with some embodiments of the technology described herein.
Figure 9B:
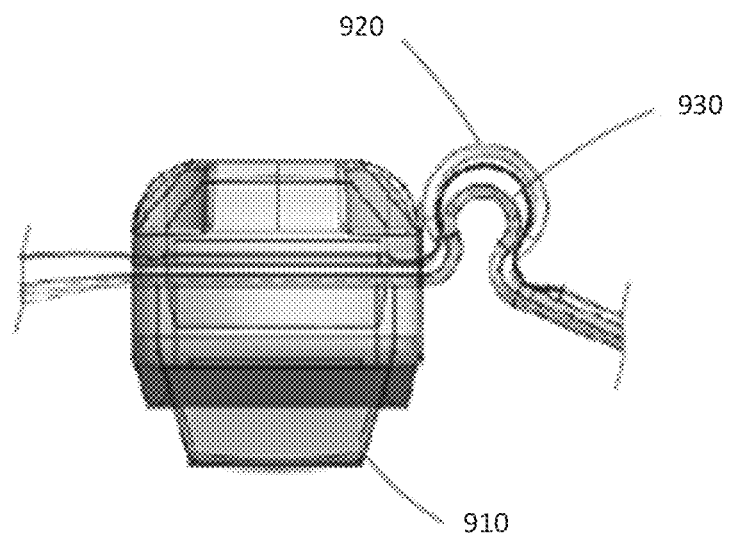
FIG. 9B is a cross-sectional view through one of the sixteen neuromuscular recording sensors illustrated in FIG. 9A.

FIG. 9A shows an alternate configuration of a wearable bioelectrical recording system with sixteen neuromuscular recording sensors 910 (e.g., sEMG sensors) arranged circumferentially around an elastic band 920 configured to be worn around a user's lower arm or wrist in accordance with some embodiments. As shown, neuromuscular recording sensors 910 are arranged circumferentially around elastic band 920. It should be appreciated that any suitable number of neuromuscular recording sensors may be used. The number and arrangement of neuromuscular recording sensors may depend on the particular application for which the wearable system is used. For example, a wearable armband or wristband can be used to generate control information for controlling an augmented reality system, a robot, controlling a vehicle, scrolling through text, controlling a virtual avatar, or any other suitable control task. As shown, the sensors may be coupled together using flexible electronics incorporated into the wireless device, FIG. 9B illustrates a cross-sectional view through one of the sensors of the wearable system shown in FIG. 9A.

In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 910 are discussed in more detail below with reference to FIGS. 10A and 10B.

FIGS. 10A and 10B illustrate a schematic diagram with internal components of a wearable system with sixteen sEMG sensors. As shown, the wearable system includes a wearable portion 1010 (FIG. 10A) and a dongle portion 1020 (FIG. 10B) in communication with the wearable portion 1010 (e.g., via Bluetooth or another suitable short range wireless communication technology). As shown in FIG. 10A, the wearable portion 1010 includes sensors 910, examples of which are described in connection with FIGS. 9A and 9B. The output of the sensors 910 is provided to analog front end 1030 configured to perform analog processing (e.g., noise reduction, filtering, etc.) on the recorded signals. The processed analog signals are then provided to analog-to-digital converter 1032, which converts the analog signals to digital signals that can be processed by one or more computer processors. An example of a computer processor that may be used in accordance with some embodiments is microcontroller (MCU) 1034 illustrated in FIG. 10A. As shown, MCU 1034 may also include inputs from other sensors (e.g., IMU sensor 1040), and power and battery module 1042. The output of the processing performed by MCU may be provided to antenna 1050 for transmission to dongle portion 1020 shown in FIG. 10B.

Dongle portion 1020 includes antenna 1052 configured to communicate with antenna 1050 included as part of wearable portion 1010. Communication between antenna 1050 and 1052 may occur using any suitable wireless technology and protocol, non-limiting examples of which include radiofrequency signaling and Bluetooth. As shown, the signals received by antenna 1052 of dongle portion 1020 may be provided to a host computer for further processing, display, and/or for effecting control of a particular physical or virtual object or objects.

Although the examples provided with reference to FIGS. 9A, 9B and FIGS. 10A, 10B are discussed in the context of interfaces with EMG sensors, it is understood that the techniques described herein for reducing electromagnetic interference can also be implemented in wearable interfaces with other types of sensors including, but not limited to, mechanomyography (MMG) sensors, sonomyography (SMG) sensors, and electrical impedance tomography (EIT) sensors.

When a user performs a motor task, such as moving their arm, a group of muscles necessary to perform the motor task is activated. When the motor task is performed while the user is wearing a wearable device that includes neuromuscular recording sensors, the neuromuscular signals recorded by the sensors on the surface of the body correspond to superimposed and spatiotemporally filtered activity of all motor units in the muscles in the group activated during performance of the motor task. The neuromuscular signals may be analyzed and mapped to control signals to control a device based on the type of movement, pose, force, or gesture that the user performs. For example, if the user performs a thumbs-up gesture with their hand, a corresponding control signal to select an object in a user interface may be generated. The mapping between sensor signals and control signals may be implemented, for example, using an inferential model trained to associate particular sensor signal inputs with control signal outputs. In some embodiments, the output of the trained inferential model may be musculoskeletal position information that describes, for example, the positions and/or forces of elements in a computer-implemented musculoskeletal model. As neuromuscular signals are continuously recorded, the musculoskeletal model may be updated with predictions of the musculoskeletal position information (e.g., joint angles and/or forces) output from the inferential model. Control signals may then be generated based on the updated musculoskeletal position information. In other embodiments, the output of the trained inferential model may be the control information itself, such that a separate musculoskeletal model is not used.

Described herein are neuromuscular (e.g., sEMG) sensor arrangements that provide improved contact between sensor electrodes and a user's body surface (e.g., skin) for improved signal detection.

According to one aspect, some embodiments described herein are directed to a neuromuscular recording sensor having electrodes that are moveable relative to the sensor housing to permit the electrodes to remain in contact with the body surface as the body portion changes conformation and/or the sensor housing moves relative to the body surface (e.g., due to a user moving their arm about their shoulder joint to wave and causing inertial forces on the housing of the neuromuscular recording sensor(s) to translate the position of an electrode relative to a portion of the surface of the user's body (e.g., skin)). In some embodiments, the electrodes may be configured in an assembly that permits them to rotate relative to the sensor housing. In some embodiments, the electrodes may be configured in an assembly that permits them to rotate and translate relative to the sensor housing. The electrodes may have at least two, at least three, at least four, at least five, or six degrees of freedom relative to the sensor housing. In some embodiments, where an electrode has five degrees of freedom relative to the sensor housing, the electrode may translate along three perpendicular axes (i.e., in three dimensions) and rotate about two of these axes relative to the sensor housing. In some embodiments, an electrode may have three degrees of freedom comprising rotation about three axes (i.e. pitch, yaw, and roll). In general, an electrode for neuromuscular recording configured in a wearable assembly or housing may rotate in any or all of the three translational axes (i.e. translating laterally along the skin in two dimensions or vertically as the skin position moves in the vertical plane relative to the housing of the neuromuscular recording system) and/or in any or all of the rotational axes (pitch, yaw, and roll).

In some embodiments, the electrodes may have a starting position in which at least a portion of the electrodes extend out of an opening of the housing, and the electrodes may be configured to move inwardly into the housing through the opening during application of force upon the electrodes. The electrodes and the housing may each be shaped to cooperate with one another to permit movement of the electrodes and to guide the electrode toward a starting position in which the electrode is seated within the housing when the contact force applied to the electrode is removed.

In some embodiments, the electrodes may be free of attachments from the sensor housing, allowing the electrodes to move relative to the housing. In other embodiments, however, the electrodes may be physically attached to the housing, but with slack and/or elasticity in the attachment arrangement (e.g., via a spring) to permit movement of the electrodes relative to the housing.

According to another aspect, in some embodiments described herein, a neuromuscular (e.g., sEMG) electrode (also referred to herein as a sensor) arrangement includes a spring element that biases the neuromuscular electrode to press against the body surface when the neuromuscular recording system that contains the neuromuscular electrode is worn by a user. The spring element may be configured to bias the electrode in a starting position in which the electrode extends outwardly from the sensor housing, while permitting the electrode to move inwardly into the housing upon application of sufficient force against the electrode.

Figure 4:
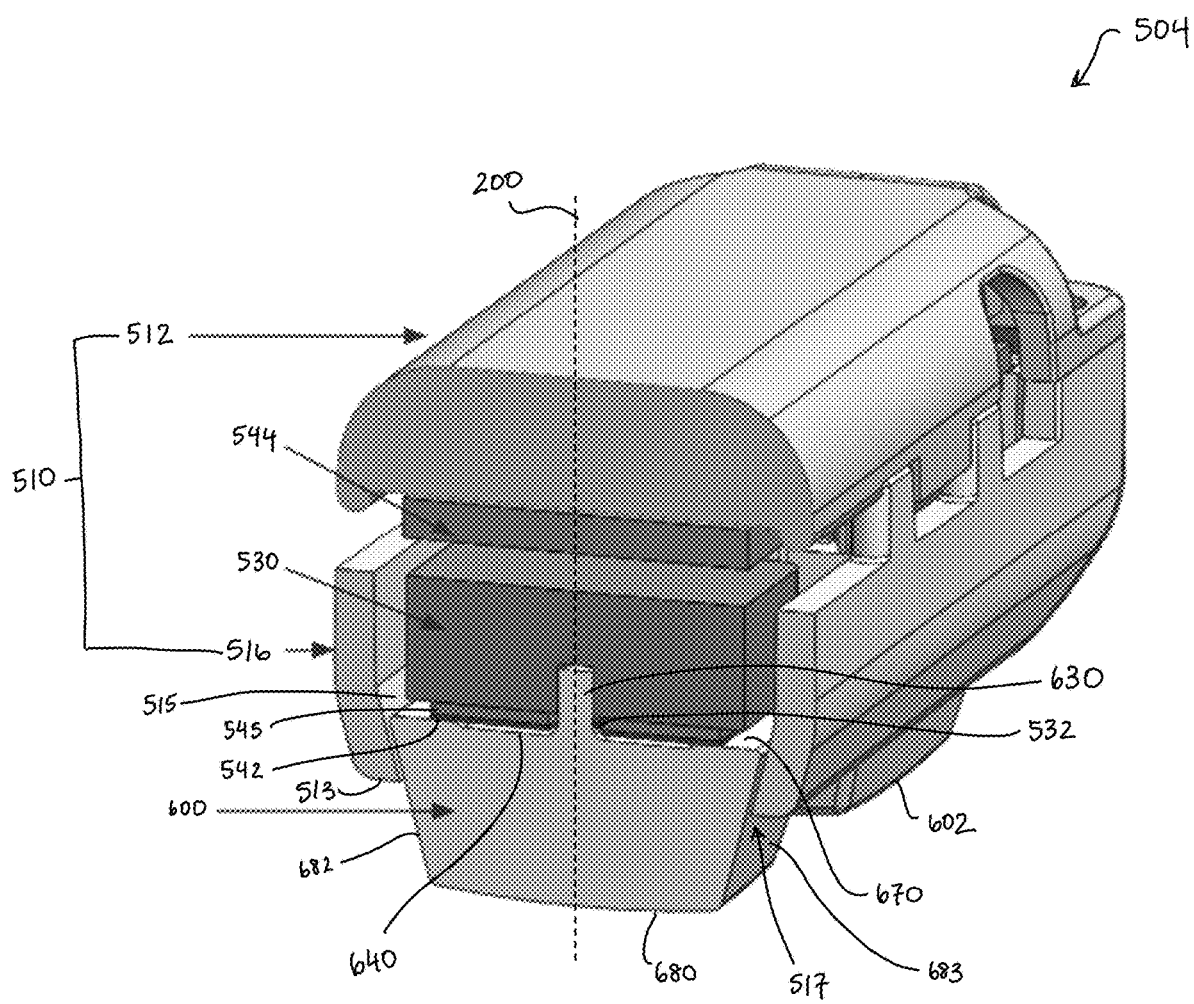
FIG. 4 depicts an illustrative embodiment of an neuromuscular recording sensor having moveable electrodes, according to some embodiments.
Figure 4:
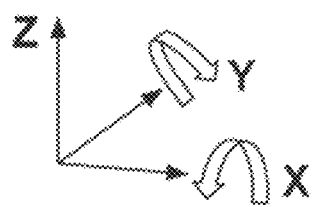

One illustrative implementation of the neuromuscular (e.g., sEMG) electrode (also referred to herein as a sensor) 504 shown in FIGS. 2, 3, and 9A-B is provided in FIG. 4, according to some embodiments. The neuromuscular recording sensor 504 includes dry electrodes 600, 602 and a housing 510, which may be made up of an upper housing 512 and a lower housing 516. The electrodes 600, 602 are moveable relative to the housing 510. In the embodiment shown in FIG. 4, the electrodes are free from attachment to the housing. The sensor housing 510 defines an opening 517 through which the electrode extends and/or moves through. The sensor includes a spring element 530 to bias the electrodes 600, 602 in a stationary starting position relative to the housing. At least a portion of the spring element may be contained within the housing 510. The inventors have recognized that other materials that function as a spring may be used instead of or in addition to the spring element 530. For example, a foam component may be positioned above the electrode within the housing.

When a force is applied to the electrodes 600, 602, e.g., due to contact of skin against the electrodes, the electrodes move relative to the housing, e.g. by rotating, translating, or both. Movement of the electrodes relative to the housing compresses the spring element 530, causing the spring element to store potential energy. When the force applied to the electrodes decreases, the spring element releases the stored potential energy and decompresses, pushing the electrodes back toward their starting positions.

In the illustrative embodiment shown in FIG. 4, the electrodes 600, 602 have five degrees of freedom relative to the housing 510. The electrodes can translate in the X, Y, and Z axes, and rotate about the X and Y axes. The vertical Z axis is oriented along the height of the sensor, the Y axis is oriented along the depth of the sensor, and the X axis is oriented along the width of the sensor. In some embodiments, the electrode has a longitudinal axis 200 that passes through a center of the electrode. The longitudinal axis 200 may bisect the electrode. The longitudinal axis is parallel to the Z axis when the electrode is in the starting position. In some embodiments, the plane of the opening 517 is parallel with the X-Y plane, and an axis normal to the plane of the opening 517 is parallel with the Z axis and with the longitudinal axis 200 of the electrode.

In some embodiments, the electrode is configured to translate relative to the housing in a direction perpendicular to the plane of the opening of the housing. In some embodiments, the electrode is configured to translate relative to the housing in a direction parallel to the plane of the opening of the housing.

In some embodiments, such as that shown in FIG. 4, the electrode is prohibited from rotation about the Z axis (yaw rotation). However, in other embodiments, the electrode is permitted to rotate about the Z axis.

Figure 5:
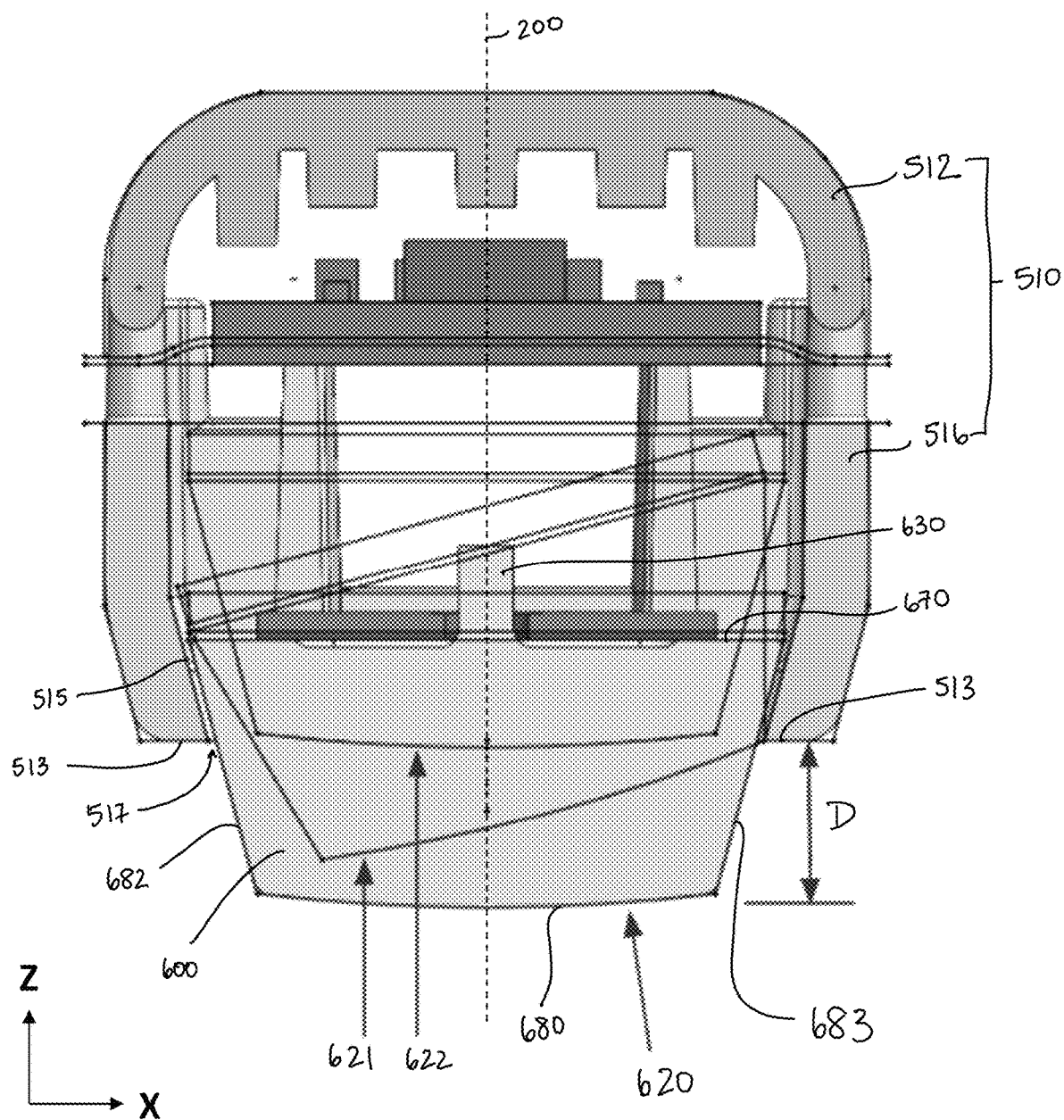
FIG. 5 depicts a cross-sectional view of the sensor shown in FIG. 4 along the X-Z plane, with the moveable electrode shown in three different positions.

FIG. 5 illustrates a few examples of different positions to which an electrode 600 in an assembly configured according to some embodiments may move during use. At rest, without any contact forces being applied to the electrode, the electrode is in the starting position 620, in which the electrode extends through the opening 517 of the housing, where a portion of the electrode is positioned within the housing 510 and a portion of the electrode is positioned outside the housing. In some embodiments, in the starting position, the portion of the electrode positioned outside the housing is larger than the portion of the electrode positioned inside the housing. In some embodiments, in the starting position, the electrode is aligned with the opening of the housing such that the longitudinal axis 200 of the electrode is parallel to the plane of the opening 517. If the opening 517 has a midpoint, the longitudinal axis of the electrode may extend through the midpoint of the opening.

Upon an application of force to the electrode, the electrode may move into an intermediate position 621 in which a greater portion of the electrode is positioned within the housing 510 as compared to the starting position 620. In the intermediate position 621 shown in FIG. 5, the electrode is both rotated and raised relative to the original starting position 620.

Finally, with an increase of force to the electrode, the electrode may move into a compressed position 622 in which an entirety of the electrode is positioned within the housing. In some embodiments, the position 622 shown in FIG. 5 is a fully raised position such that the electrode cannot move any further into the housing. However, in other embodiments, the electrode is able to move still further into the housing. In yet other embodiments, when the electrode is in the fully raised position, a portion of the electrode remains outside the housing.

Distance D shown in FIG. 5 is the distance of travel of the electrode from the starting position 620 to the compressed position 622. Distance D is also the distance from the bottom surface 680 of the electrode to the bottom surface 513 of the housing 510. In some embodiments, distance D is also the maximum travel distance of the electrode. The inventors recognize that larger values of D permit a larger range of motion of the electrode in the Z-dimension upon a force being exerted upon the electrode (e.g., due to a change in the relative force between the portion of a user's body underlying the electrode and the housing of a wearable neuromuscular recording device that contains the electrode), while also enabling electrode contact to be maintained if the housing of the wearable neuromuscular recording apparatus is positioned such that a particular electrode of the apparatus is relatively far (e.g., having a distance<D) from the surface of the body (e.g., skin). The inventors have recognized that a larger value of D requires a larger housing for that section of the wearable neuromuscular recording device to permit movement of the electrode into the housing up to a distance of D. The inventors have recognized that the value of D should be selected to balance the various constraints listed above for a given form factor of a neuromuscular recording apparatus and portion of the body on which it is intended to be worn.

In some embodiments, different electrodes of a neuromuscular recording device that includes a plurality of electrodes may be configured with different values of D based on the expected range of motion required for that electrode given the form factor of the apparatus and the portion of the body on which it is meant to be worn. For example, an apparatus for neuromuscular recording on the wrist may be configured with electrodes having a larger distance D for electrodes overlying the top and bottom of the wrist and a smaller distance D for electrodes overlying the sides of the wrist, because relative movement of tissue is generally larger at the top and bottom of the wrist where soft tissue (tendons, muscles, etc.) is present than for the side of the wrist where bones are present with less soft tissue.

In some embodiments, distance D may be at least about 0.01 mm, at least about 0.1 mm, at least about 1 mm, at least about 1.2 mm, at least about 1.4 mm, at least about 1.6 mm, at least about 1.8 mm, at least about 2 mm, at least about 2.2 mm, or at least about 2.4 mm. In some embodiments, distance D may be less than or equal to about 4 mm, less than or equal to about 3 mm, less than or equal to about 2.8 mm, less than or equal to about 2.6 mm, less than or equal to about 2.4 mm, less than or equal to about 2.2 mm, less than or equal to about 2 mm, or less than or equal to about 1.8 mm. Combinations of the above-referenced ranges are also possible. For example, in some embodiments, the distance D may be about 1 mm to about 4 mm, or about 1.2 mm to about 3 mm, or about 1.4 mm to about 2.6 mm, or about 1.6 mm to about 2.4 mm, or about 1.8 mm to about 2.2 mm, or about 2 mm.

In some embodiments, the electrode must move a threshold distance in the Z direction along the height of the sensor (e.g. in a direction perpendicular to the plane of the opening into the housing) before the electrode is free to translate and rotate on the other two axes perpendicular to the Z axis. In other embodiments, no threshold distance is needed.

The electrodes may be configured to contour to the body, e.g., by reaching into a valley or cleft between muscles and maintain contact while the user moves and contracts muscles in the body part to which the electrodes are coupled to, e.g., the arm. Thus, the inventors have recognized that the assemblies of neuromuscular recording devices that permit movement (e.g., translation and/or rotation) of one or more electrodes as described herein must have dynamics that are responsive (e.g., via appropriate selection of spring constants of materials) at the timescales of movement of the musculoskeletal system (e.g., hundreds of milliseconds to seconds).

In some embodiments, the electrode 600 has a contact surface 680 that is configured to make contact with the body surface, e.g., skin. In some embodiments, the contact surface 680 may have a surface that is curved in a convex shape to help the electrode roll along the body surface during muscle movements to decrease sliding artifacts. The surface may be contoured in a variety of ways, such as to avoid hair, and to move with the skin. For example, instead of having a uniformly curved convex shape, the surface of the electrode may have some sections that are concave or otherwise have a different curvature/contour to facilitate movement relative to the skin.

It should be appreciated that different degree of freedom arrangements are contemplated. In some embodiments, an electrode rotates relative to the sensor housing. In some embodiments, an electrode has at least two degrees of freedom relative to the sensor housing. For example, the electrode may translate and rotate, or, the electrode may translate along two axes, or, the electrode may rotate about two axes. In some embodiments, an electrode has at least two degree of freedom, or, at least three degrees of freedom, or at least four degrees of freedom, or at least five degrees of freedom, or six degrees of freedom relative to the housing.

In some embodiments, the sensor includes a flexible circuit that permits movement of the electrode relative to the housing. In embodiments with the sensor having a plurality of electrodes, the flexible circuit connects the electrodes together. In some embodiments, a portion of the circuit includes one or more rigid printed circuit boards ("PCBs") and a portion of the circuit includes one or more flexible PCBs. In some embodiments, a rigid PCB is fixed to each of the electrodes, and the flexible PCBs connect the rigid PCBs to one another. In some embodiments, the flexible PCB is also connected to each of the electrodes. The inventors recognize that the use of one or more flexible PCBs in the mechanical assemblies for a wearable neuromuscular recording device as described herein enable movement of electrodes relative to rigid elements and the housing, so that the electrode is able to maintain contact with the skin as the wearable device moves relative to the user's body surface (e.g., skin).

In the illustrative embodiment shown in FIG. 4, the sensor 504 has a rigid PCB 545 and a flexible PCB 542 attached to the electrode 600 on the longer base 670 side of the electrode. The sensor 504 also includes another rigid PCB 544 in an upper portion of the sensor, above the spring element 530. The flexible PCB 542 may also connect to the upper rigid PCB 544.

Figure 6A:
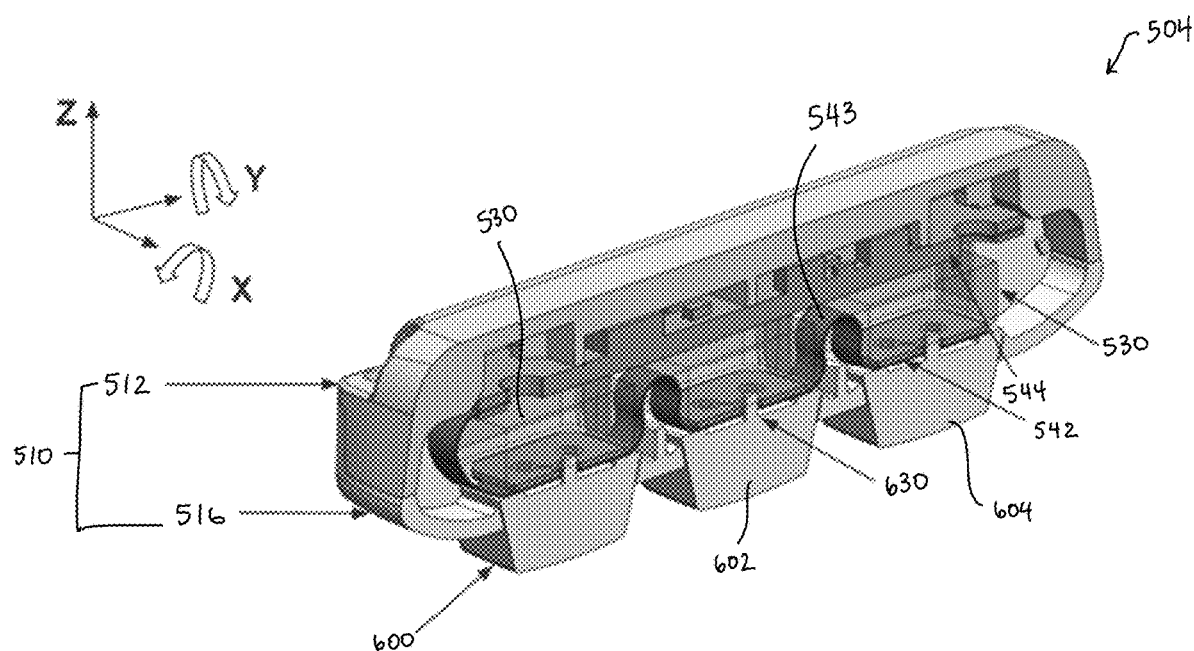
FIG. 6A depicts a perspective section view of the sensor shown in FIG. 4.
Figure 6B:
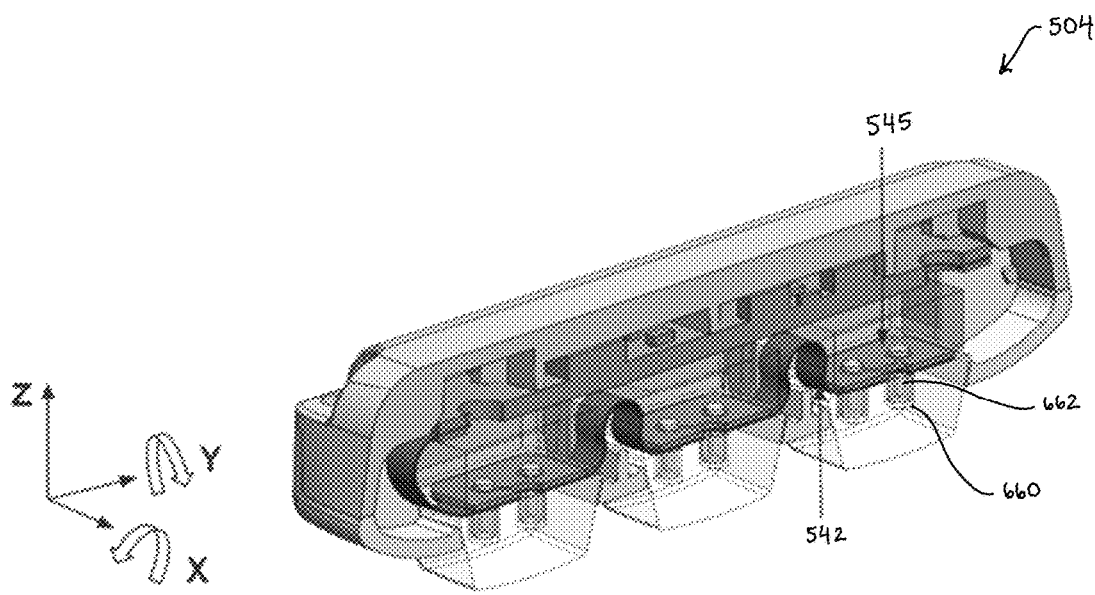
FIG. 6B depicts the neuromuscular recording sensor of FIG. 6A with the electrodes shown in phantom.

The illustrative embodiment shown in FIGS. 6A and 6B shows an example of how a flexible circuit may be used to connect the electrodes together. As best seen in FIG. 6A, a rigid PCB 544 may be attached to each of the electrodes, and a flexible PCB 542 connects each of the rigid PCBs 544 together. The flexible PCB is also connected to each of the electrodes 600, 602, 604, with the flexible PCB between each of the electrodes and their associated rigid PCB. The flexible PCB also connects to an upper rigid PCB 544.

The flexible PCB may include portions of slack 543 between the electrodes that allow for independent movement between the electrodes. The portions of slack may form a curved arc shape when each of the electrodes are in a starting position. When one electrode moves relative to another, the portions of slack may change conformation from a curved shape to more of a linear shape.

In some embodiments, the electrodes are manufactured as a single, monolithic piece of metal, and connected to the flexible circuit. The electrodes may be soldered to the flexible circuit using fabrication techniques such as wave or reflow soldering, or pin/socket connectorization.

In the illustrative embodiment shown in FIG. 6B, the electrodes 600, 602, 604 each include a socket 660. For each of the electrodes, a pin 662 is passed through the socket of the electrode and through the rigid and flexible PCBs, connecting the electrodes to the PCBs.

In some embodiments, the electrode interacts with the spring element via a pin and socket relationship. For example, the electrode may have a protruding post, and the spring element may have a socket that is sized to receive the post of the electrode. In some embodiments, the diameter of the socket is larger than the diameter of the post such that there is some clearance around the post when the post sits within the socket. In some embodiments, the diameter of the socket is equal to the diameter of the post. In some embodiments, the diameter of the socket is smaller than the diameter of the post to create an interference fit between the socket and the post.

In the illustrative embodiment shown in FIG. 4, the electrode 600 has a post 630 that is received within a socket 532 of the spring element. In some embodiments, the post is integrally formed with the electrode as a single, monolithic component.

In some embodiments, a thermal relief is positioned between the electrode and the PCB. A thermal relief may be, for example, an indentation or cutout in a surface of an electrode. For example, as shown in the FIG. 4 embodiment, a thermal relief 640 is an indentation in the 670 surface of the electrode and is located between the electrode 600 and the PCBs 542 and 545. The thermal relief may be located at the surface of the electrode that faces the PCBs. The thermal relief may span across an area that is smaller than the area of overlap between the PCBs and the electrode, such that direct contact may be made between the electrode and the PCBs.

In some embodiments, the electrode and post is soldered to the PCBs of the circuit. The thermal relief 640 may help to dissipate heat from the soldering process to decrease the amount of heat that is transferred to the PCBs. In some embodiments, movement of the electrode may cause the post to heat up, e.g. due to friction. The thermal relief 640 of the electrode may serve to dissipate the heat from the post to decrease the amount of heat that is transferred to the PCBs. In some embodiments, spring element 530 may be made of an insulating material that absorbs heat from the post.

A wearable device may incorporate a plurality of neuromuscular recording (e.g., sEMG) sensors having moveable electrodes. Each of the sensors may be electrically connected with one another. The housings of each of the sensors may be coupled to one another to form the wearable device. In some embodiments, the housings of adjacent sensors may be attached to one another while remaining moveable relative to one another. The housings of adjacent sensors may have one, two, three, four, five, or six degrees of freedom relative to one another. In some embodiments, the housings of adjacent sensors are attached to one another via a hinge and are free to pivot relative to one another. In some embodiments, the housings of adjacent sensors are attached to one another via an elastic band and are free to pivot and translate relative to one another.

In the illustrative embodiment shown in FIG. 2, adjacent sensor housings are attached to one another via joints 501. Sensors are connected to one another via joints to form a curveable array of sensors extending from a first end 410 to a second end 420. To form a closed loop, a band 502 may be used to connect the ends 410, 412 of the arc of sensors. The joints 501 between the sensors may have the ability to permit adjacent sensors to pivot relative to one another and/or be pulled away from one another. The band may form a complete loop that is coupled to the array of sensors, as best seen in FIG. 3. The band 502 may have elastic properties to create a biasing force that provides continuous pressure of the electrodes against the wearer's body surface, e.g., the skin of the wearer's arm. This continuous pressure provided by the elastic band is opposed by the biasing force provided by the spring elements in each of the sensors. The pressure of the electrodes against the body surface created by the elastic band may cause the electrodes of the sensors 504 to move relative to the sensor housings, causing the spring elements of the sensors to compress. As the wearer moves and/or contracts muscles in the body part on which the device is worn, the continuous pressure provided by the elastic band, along with the ability of the electrodes to move relative to the sensor housings with the moving skin, help to keep the electrodes in contact with the skin. In some embodiments, the housings themselves and the joints that connect them form a wearable device such that a separate band coupled to the housings is not required.

The spring element 530 is a component that is capable of storing potential energy. In the illustrative embodiments shown in the figures, the spring element is an elastically compressible block of material. Examples of possible materials for the spring element include, but are not limited to, neoprene, EPDM, foam, silicone rubber, natural rubber, synthetic rubber, sponge rubber, foam rubber, other rubbers, PVC, thermoplastic polymers. The spring element may take on different forms other than a block of material. For example, the spring element may be a helical spring such as a coil spring, tapered spring, or hourglass spring, or the spring element may be a leaf spring, torsion spring, disc spring, clock spring, flat spring, wave spring, hourglass spring, a stretchable fabric, an elastically compressible component, or any other component that can be used to store potential energy.

The spring element may be a single component, as with the compressible block shown in the figures, or may be a collection of multiple components, such as a plurality of spring coils spread out over an area of the electrode, e.g., one on each corner of the upper surface of the electrode and one or more coils in a central region of the upper surface of the electrode.

Figure 11A:
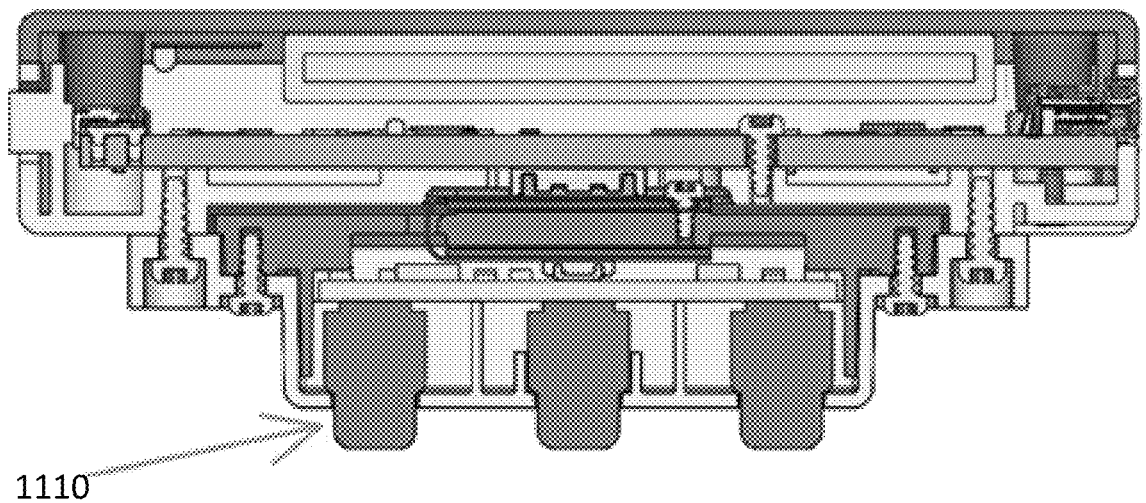
FIG. 11A shows a cross-sectional view through a neuromuscular recording sensor and its associated sensor housing, in accordance with some embodiments of the technology described herein.
Figure 11B:
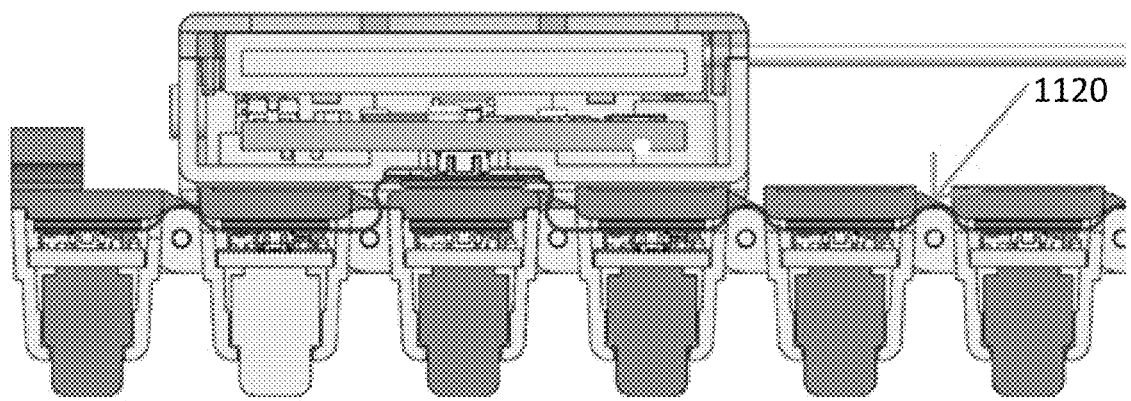
FIG. 11B shows a cross-sectional view through a plurality of neuromuscular recording sensors coupled via hinge structures, in accordance with some embodiments of the technology described herein.

As discussed above, in some embodiments, the housings of adjacent sensors are attached to one another via a hinge and are free to pivot relative to one another. In some embodiments, the electrode within the sensor housing only has one degree of freedom relative to the sensor housing, with extra degrees of freedom provided by the hinge connecting adjacent sensors. For example, a spring element 1110 oriented in the axis normal to the sensor housing may provide the single degree of freedom for the electrode relative to the housing as shown, for example, in FIG. 11A. As shown in FIG. 11B, hinge 1120 may provide additional degree(s) of freedom. In such an arrangement, the combination of the single degree of freedom provided by the spring element 1110 and the additional one or more degrees of freedom provided by the hinge 1120 provide a wearable biosensor recording device with multiple degrees of freedom to enable electrodes to remain in contact with the body surface (e.g., the skin) during movements and/or muscle contractions, as described herein.

In some embodiments, the spring element may be made of a material having a Young's Modulus of at least about 0.5 MPa, at least about 1 MPa, at least about 1.5 MPa, at least about 2 MPa, at least about 2.5 MPa, at least about 3 MPa, at least about 3.5 MPa, at least about 4 MPa, at least about 4.5 MPa, at least about 5 MPa, at least about 5.5 MPa, at least about 6 MPa, at least about 6.5 MPa, at least about 7 MPa, at least about 7.5 MPa, at least about 8 MPa, at least about 8.5 MPa, at least about 9 MPa, at least about 9.5 MPa, or at least about 10 MPa. In some embodiments, the spring element may be made of a material having a Young's Modulus of less than or equal to about 10 MPa, less than or equal to about 9.5 MPa, less than or equal to about 9 MPa, less than or equal to about 8.5 MPa, less than or equal to about 8 MPa, less than or equal to about 7.5 MPa, less than or equal to about 7 MPa, less than or equal to about 6.5 MPa, less than or equal to about 6 MPa, less than or equal to about 5.5 MPa, less than or equal to about 5 MPa, less than or equal to about 4.5 MPa, less than or equal to about 4 MPa, less than or equal to about 3.5 MPa, less than or equal to about 3 MPa, less than or equal to about 2.5 MPa, less than or equal to about 2 MPa, less than or equal to about 1.5 MPa, or less than or equal to about 1 MPa. Combinations of the above-referenced ranges are also possible. For example, in some embodiments, the spring element may be made of a material having a Young's Modulus of about 0.5 MPa to about 10 MPa, or about 1.5 MPa to about 9 MPa, or about 2.5 MPa to about 8 MPa, or about 3.5 MPa to about 7 MPa, or about 5 MPa to about 6.5 MPa, or about 5 to 7 MPa, or about 6 MPa.

In some embodiments, the spring element may have a spring constant k of at least about 1.5 N/mm, 2 N/mm, 2.5 N/mm, 3 N/mm, 3.5 N/mm, 3.75 N/mm, 4 N/mm, 4.5 N/mm, or 5 N/mm. In some embodiments, the spring element may have a spring constant k of less than or equal to about 10 N/mm, 9 N/mm, 8 N/mm, 7 N/mm, 6 N/mm, 5 N/mm, 4 N/mm, 3.75 N/mm, 3.5 N/mm, 3 N/mm, or 2 N/mm. Combinations of the above-referenced ranges are also possible. For example, in some embodiments, the spring element may have a spring constant k of about 1.5 N/mm to about 10 N/mm, or about 2 N/mm to about 8 N/mm, or about 2.5 N/mm to about 6 N/mm, or about 3 N/mm to about 4 N/mm, or about 3.5 N/mm to about 4 N/mm, or about 3.75 N/mm.

In some embodiments, the spring element may behave as a nonlinear spring.

In some embodiments, the spring element may provide different spring forces and/or mechanical resistances on different axes. This may be accomplished by a spring element that is a single component, or a spring element that is a collection of components.

In some embodiments, the spring element is unattached to the electrode and/or to the housing. In some embodiments, the spring element is not physically attached to any components of the sensor. Instead, the spring element is free-floating. The spring element may be constrained from movement due to the physical presence of other components arranged on either side and/or surrounding the spring element. For example, in the embodiment shown in FIG. 4, the spring element 530 is sandwiched between rigid PCB 544 and rigid PCB 545. In some embodiments, the sides of the spring element may be constrained from lateral movement by the inner surfaces of the housing.

According to some aspects, in some embodiments, physical interaction between the housing and the electrode determines the starting position of the electrode. The housing may be shaped to accommodate the shape of the electrode such that the housing guides the electrode back into its starting position when the electrode is no longer subjected to a contact force. In some embodiments, the electrode has only a single starting position.

In some embodiments, the housing has an inner surface with sloped walls that serve as a funnel to guide the electrode back toward its starting position. For example, in the illustrative embodiment shown in FIGS. 4 and 5, the housing 510 has inner surfaces 515 adjacent to the opening 517 into the housing. The inner surfaces are angled inwardly toward one another to create a funnel effect. To cooperate with these inner surfaces, the electrode has side surfaces 682, 683 that are also sloped inwardly toward one another. The side surfaces of the electrode may be sloped at a same angle as that of the inner walls of the housing. As a result, when the spring element releases potential energy and pushes the electrode back out of the housing toward the starting position, the inner surfaces of the housing may help to properly seat the electrode within the opening 517 of the housing into the starting position.

The electrodes shown in FIGS. 4-6B have a trapezoidal prism shape. In some embodiments, when the electrode is in the starting position, the longer base 670 of the trapezoidal prism is located within the housing 510 and the shorter base is the contact surface 680, which is located outside the housing, and the two side surface 682 and 683 connect the longer base 670 to the shorter base/contact surface 680. Note that, in embodiments where contact surface 680 is curved in a convex shape, the approximate shape of the electrode is still considered to be trapezoidal even though the two bases 670, 680 are not technically parallel to one another.

It should be appreciated that different electrode shapes and housing shapes are contemplated. For example, the electrode may have a cross-sectional shape that is or is approximately trapezoidal, triangular, rectangular, square, semicircular, semi-elliptical, domed, round, or any other suitable shape. The electrode may be or may approximate the shape of: a cylinder, prism (including rectangular prism and trapezoidal prism), cube, cuboid, conical frustum, square frustum, pentagonal frustum, a hemisphere, a dome, an elongated dome, egg-shaped, an ellipsoid, a semi-ellipsoid, or any other suitable shape.

Figure 7A:
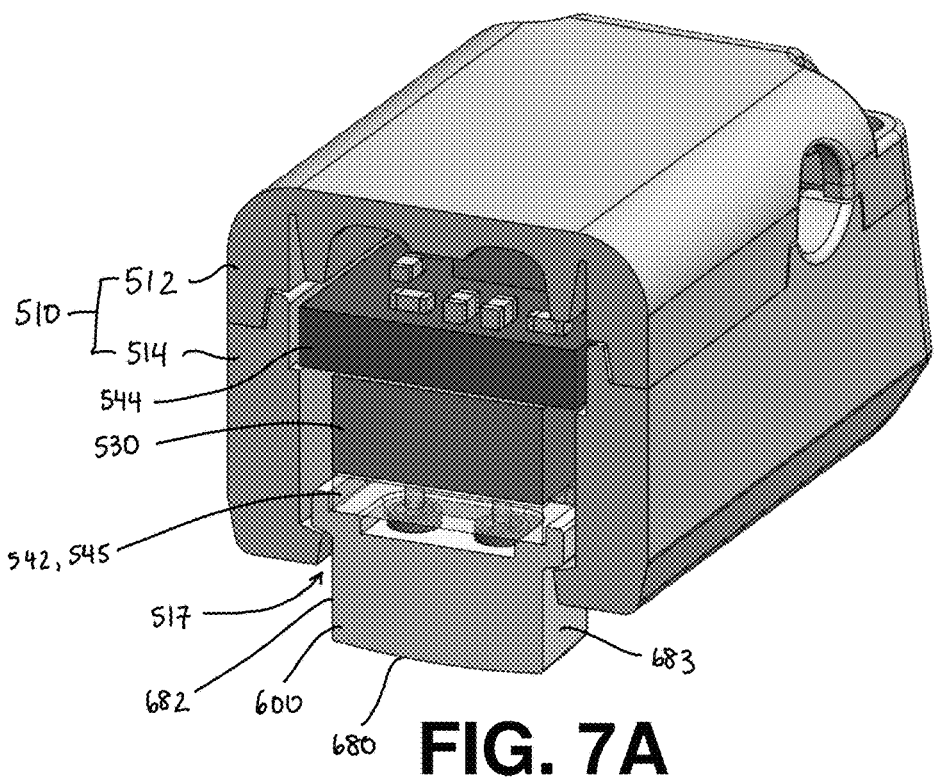
FIG. 7A depicts an illustrative embodiment of a neuromuscular recording sensor according to an alternative embodiment.
Figure 7B:
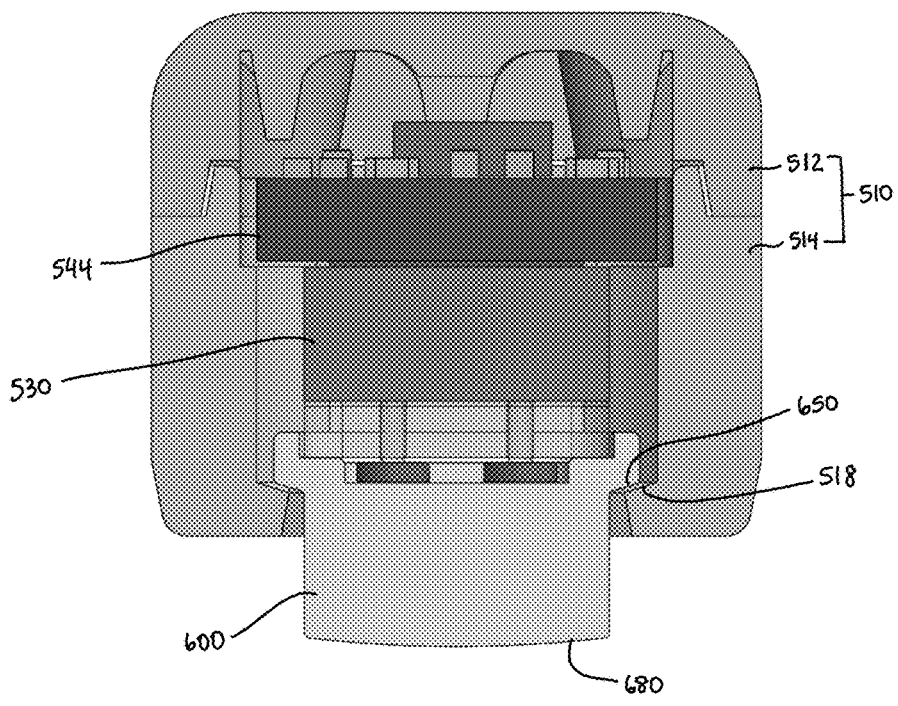
FIG. 7B depicts a cross-sectional view of the neuromuscular recording sensor shown in FIG. 7A.

In one illustrative embodiment shown in FIGS. 7A and 7B, an electrode 600 may have side surfaces 682, 683 that are parallel to one another rather than sloped. As seen in FIG. 7B, the electrode 600 has an approximately rectangular cross-section, with the contact surface 680 being outwardly curved in a convex shape.

In the embodiment shown in FIGS. 7A and 7B, without sloped side surfaces to provide a funneling effect, the electrode may include a different feature to permit the electrode to be seated within the opening of the housing. The electrode includes shoulders 650 that interact with the housing to seat the electrode in place. The housing has contact surfaces in the form of ledges 518 protruding from the inner surface of the housing, where the ledges are sized and shaped to receive the shoulders 650 of the electrode. As seen in FIG. 7B, with the electrode 600 in the starting position, the shoulders 650 of the electrode are pushed by the spring element 530 against the ledges 518 of the housing to seat the electrode in place within the opening 517 of the housing. The shoulders of the electrode may protrude outwardly beyond the side surfaces 682, 683 of the electrode, as shown in FIG. 7B.

Figure 8A:
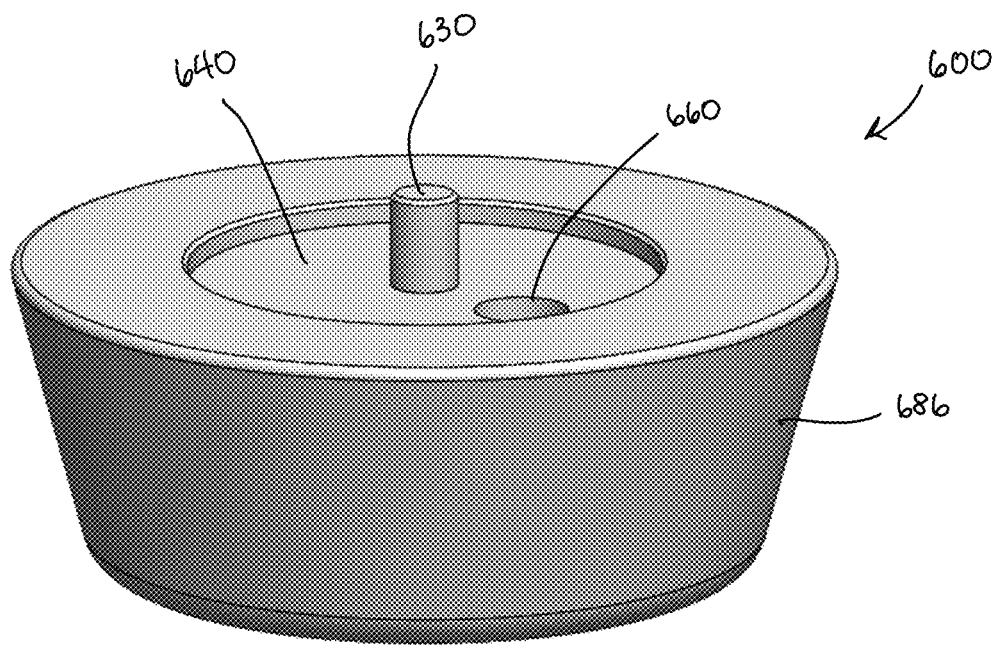
FIG. 8A depicts an illustrative embodiment of an electrode for neuromuscular recording sensor according to an alternative embodiment.
Figure 8B:
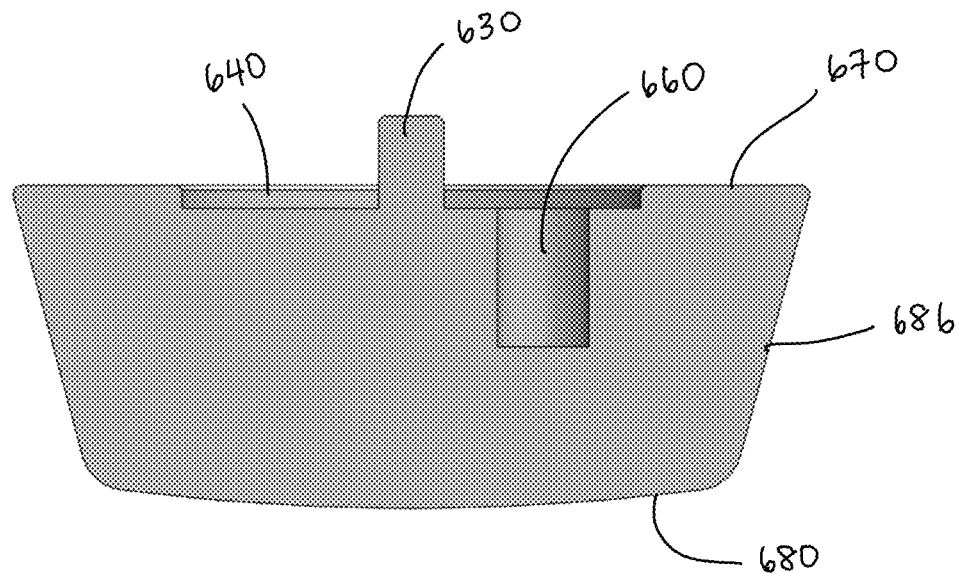
FIG. 8B depicts a cross-sectional view of the neuromuscular recording sensor shown in FIG. 8A.

In another illustrative embodiment shown in FIGS. 8A and 8B, electrode 600 has a round form. The electrode has one continuous sidewall 686 that extends around the entire electrode. The electrode 600 has an approximately frustoconical shape, with a longer base 670 and a shorter base 680 that serves as a contact surface. The contact surface 680 may be curved outwardly in a convex shape. As seen in FIG. 8B, the cross-sectional shape of the electrode is approximately trapezoidal.

A housing shaped to accommodate a frustoconical electrode such as the one shown in FIGS. 8A and 8B may have a circular inner wall surface that is slanted to match the angle of the sidewall 686 of the electrode. The opening defined by the housing through which the electrode extends and moves may be circular.

It should be appreciated that different electrode shapes may be used for the sensor, and the sensor housing may have different conformations to accommodate and guide movement of such electrodes.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

Various aspects of the apparatus and techniques described herein may be used alone, in combination, or in a variety of arrangements not specifically discussed in the embodiments described in the foregoing description and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The invention claimed is:

1. A wearable bioelectrical sensing device comprising:
   a plurality of electrodes including a first electrode, a second electrode, a third electrode, and a fourth electrode;
   a first housing containing at least a portion of the first electrode and at least a portion of the second electrode, the first housing including at least one angled portion that guides one or more corresponding angled portions of the first and second electrodes into a starting position within the first housing, wherein the first and second electrodes are free to translate along the X, Y, and Z axes within the first housing, the X axis being oriented along the width of the first and second electrodes, the Y axis being oriented along the depth of the first and second electrodes, and the Z axis being oriented along the height of the first and second electrodes;
- a second housing containing at least a portion of the third electrode and at least a portion of the fourth electrode, each of the third and fourth electrodes being configured to rotate relative to the second housing,
  - wherein the first housing and the second housing are coupled to each other in an arrangement that enables the first, second, third, and fourth electrodes to contact the body part of a user when the wearable bioelectrical sensing device is worn around the body part of the user;
- a first flexible circuit electrically connecting the first electrode to the second electrode within the first housing;
- a second flexible circuit electrically connecting the third electrode to the fourth electrode within the second housing; and
- a spring element configured to bias the first electrode toward the starting position of the first electrode.

2. The wearable bioelectrical sensing device of claim 1, wherein at least a portion of the spring element is contained within the first housing.

3. The wearable bioelectrical sensing device of claim 1, wherein the spring element comprises foam or neoprene.

4. The wearable bioelectrical sensing device of claim 1, wherein the first housing defines an opening and, in the starting position, the first electrode extends through the opening of the first housing.

5. The wearable bioelectrical sensing device of claim 1, wherein a minimum specified distance between the first housing and the first electrode is determined based on an expected range of motion for the first electrode.

6. The wearable bioelectrical sensing device of claim 1, wherein an opening in the first housing allows the first electrode to rotate relative to the first housing about the X and Y axes.

7. The wearable bioelectrical sensing device of claim 6, wherein a post in the first housing prohibits the first electrode from rotating about the Z axis relative to the spring element.

8. The wearable bioelectrical sensing device of claim 7, wherein the first housing defines an opening and, in the starting position, the first electrode extends through the opening of the first housing.

9. The wearable bioelectrical sensing device of claim 1, further comprising a post attached to the first electrode and extending through the spring element.

10. The wearable bioelectrical sensing device of claim 9, wherein the post is integrally formed with the first electrode as a single, monolithic component.

11. The wearable bioelectrical sensing device of claim 1, wherein a first specified range of movement exists between the first electrode relative to the first housing and a second specified range of movement exists between the third electrode relative to the second housing, and wherein the first specified range of movement of the first electrode relative to the first housing is different than the second specified range of movement of the third electrode relative to the second housing.

12. The wearable bioelectrical sensing device of claim 1, wherein a cross section of the first electrode has a shape selected from the group consisting of a trapezoidal shape, a rectangular shape, a circular shape, and an elliptical shape.

13. The wearable bioelectrical sensing device of claim 12, wherein the first electrode has a curved contact surface.

14. The wearable bioelectrical sensing device of claim 1, further comprising a band coupled to the first housing and the second housing to provide the arrangement that enables the first, second, third, and fourth electrode to contact the body part of the user when the wearable bioelectrical sensing device is worn around the body part of the user.

15. The wearable bioelectrical sensing device of claim 1, further comprising a hinge coupling the first housing and the second housing to provide the arrangement that enables the first, second, third, and fourth electrode to contact the body part of the user when the wearable bioelectrical sensing device is worn around the body part of the user.

16. A wearable bioelectrical sensing device, comprising:
- a plurality of electrodes including a first electrode, a second electrode, a third electrode, and a fourth electrode;
- a first housing containing at least a portion of the first electrode and at least a portion of the second electrode, each of the first and second electrodes being movable relative to the first housing with at least one degree of freedom, the first housing including least one angled portion that guides one or more corresponding angled portions of the first and second electrodes into a starting position within the first housing, wherein the first and second electrodes are free to translate along the X, Y, and Z axes within the first housing, the X axis being oriented along the width of the first and second electrodes, the Y axis being oriented along the depth of the first and second electrodes, and the Z axis being oriented along the height of the first and second electrodes;
- a second housing containing at least a portion of the third electrode and at least a portion of the fourth electrode, each of the third and fourth electrodes being movable relative to the second housing with at least one degree of freedom such that each of the third electrode and the fourth electrode is movable from a starting position to a different position relative to the second housing,
  - wherein the first housing and the second housing are coupled to each other in an arrangement that enables the first, second, third, and fourth electrode to contact the body part of a user when the wearable bioelectrical sensing device is worn around the body part of the user;
- a first flexible circuit electrically connecting the first electrode to the second electrode within the first housing;
- a second flexible circuit electrically connecting the third electrode to the fourth electrode within the second housing; and
- a spring element configured to bias the first electrode toward the starting position of the first electrode.

17. The wearable bioelectrical sensing device of claim 16, wherein an opening in the first housing allows the first electrode to move relative to the first housing with five degrees of freedom, and wherein the five degrees of freedom comprise translation along the X axis, the Y axis, and the Z axis, and rotation about the X and Y axis, wherein the X axis, the Y axis, and the Z axis are perpendicular to one another.

18. The wearable bioelectrical sensing device of claim 16, further comprising a hinge coupling the first housing and the second housing to provide the arrangement that enables the first, second, third, and fourth electrode to contact the body part of the user when the wearable bioelectrical sensing device is worn around the body part of the user.

19. The wearable bioelectrical sensing device of claim 18, wherein the hinge is configured to enable the first electrode to move with at least one additional degree of freedom.

20. A method of producing a wearable bioelectrical sensing device, the method comprising:
assembling a first housing containing at least a portion of a first electrode and at least a portion of a second electrode, the first housing including at least one angled portion that guides one or more corresponding angled portions of the first and second electrodes into a starting position within the first housing, wherein the first and second electrodes are free to translate along the X, Y, and Z axes within the first housing, the X axis being oriented along the width of the first and second electrodes, the Y axis being oriented along the depth of the first and second electrodes, and the Z axis being oriented along the height of the first and second electrodes,
assembling a second housing containing at least a portion of a third electrode and at least a portion of a fourth electrode,
wherein the first housing and the second housing are coupled to each other in an arrangement that enables the first, second, third, and fourth electrodes to contact the body part of a user when the wearable bioelectrical sensing device is worn around the body part of the user;
assembling a first flexible circuit electrically connecting the first electrode to the second electrode within the first housing;
assembling a second flexible circuit electrically connecting the third electrode to the fourth electrode within the second housing; and
assembling a spring element configured to bias the first electrode toward a starting position of the first electrode.

21. The method of claim 20, further comprising:
assembling the spring element contained within the first housing, wherein the spring element is capable of rotating the first electrode relative to the first housing, and wherein the spring element is configured to bias the first electrode toward the starting position.

22. The method of claim 20, wherein the first electrode is capable of rotating relative to the first housing about a first axis, and wherein the first electrode is capable of rotating relative to the first housing about the X axis, and wherein the first electrode is capable of rotating relative to the first housing about the Y axis that is perpendicular to the X axis while the first electrode maintains contact with the skin throughout the rotation.

23. A system comprising:
a first electrode, a second electrode, a third electrode, and a fourth electrode;
a first housing containing at least a portion of the first electrode and at least a portion of the second electrode, the first housing including at least one angled portion that guides one or more corresponding angled portions of the first and second electrodes into a starting position within the first housing, wherein the first and second electrodes are free to translate along the X, Y, and Z axes within the first housing, the X axis being oriented along the width of the first and second electrodes, the Y axis being oriented along the depth of the first and second electrodes, and the Z axis being oriented along the height of the first and second electrodes,
a second housing containing at least a portion of the third electrode and at least a portion of the fourth electrode, each of the third and fourth electrodes being configured to rotate relative to the second housing,
wherein the first housing and the second housing are coupled to each other in an arrangement that enables the first and second electrodes to contact the body part of the user when the wearable bioelectrical sensing device is worn around the body part of the user;
a first flexible circuit electrically connecting the first electrode to the second electrode within the first housing;
a second flexible circuit electrically connecting the third electrode to the fourth electrode within the second housing; and
a spring element configured to bias the first electrode toward the starting position of the first electrode.

24. The system of claim 23, wherein the first electrode is configured to move with five degrees of freedom relative to the first housing, wherein the five degrees of freedom comprise translation along the X axis, the Y axis, and the Z axis, and rotation about the X and Y axis, wherein the X axis, the Y axis, and the Z axis are perpendicular to one another.

* * * * *